US011123428B2

(12) United States Patent
Garner et al.

(10) Patent No.: US 11,123,428 B2
(45) Date of Patent: Sep. 21, 2021

(54) INACTIVATING BACTERIA WITH ELECTRIC PULSES AND ANTIBIOTICS

(71) Applicants: Purdue Research Foundation, West Lafayette, IN (US); Nanovis, LLC, Columbia City, IN (US)

(72) Inventors: Allen Lawrence Garner, West Lafayette, IN (US); Ram Anand Vadlamani, West Lafayette, IN (US); David Alan Detwiler, Columbia City, IN (US)

(73) Assignees: Purdue Research Foundation, West Lafayette, IN (US); Nanovis, LLC, Columbia City, IN (US)

( * ) Notice: Subject to any disclaimer, the term of this patent is extended or adjusted under 35 U.S.C. 154(b) by 0 days.

(21) Appl. No.: 16/991,284

(22) Filed: Aug. 12, 2020

(65) Prior Publication Data
US 2020/0368351 A1 Nov. 26, 2020

Related U.S. Application Data

(63) Continuation of application No. PCT/US2019/017761, filed on Feb. 13, 2019.

(60) Provisional application No. 62/630,219, filed on Feb. 13, 2018.

(51) Int. Cl.
| | | |
|---|---|---|
| *A61K 31/496* | (2006.01) | |
| *A61K 31/341* | (2006.01) | |
| *A61K 31/575* | (2006.01) | |
| *A61K 31/702* | (2006.01) | |
| *A61K 31/5377* | (2006.01) | |
| *A61K 38/14* | (2006.01) | |
| *A61K 41/00* | (2020.01) | |
| *A61K 31/7048* | (2006.01) | |
| *A61N 1/32* | (2006.01) | |
| *C12N 13/00* | (2006.01) | |

(52) U.S. Cl.
CPC ........ *A61K 41/0023* (2013.01); *A61K 31/341* (2013.01); *A61K 31/496* (2013.01); *A61K 31/5377* (2013.01); *A61K 31/575* (2013.01); *A61K 31/702* (2013.01); *A61K 31/7048* (2013.01); *A61K 38/14* (2013.01); *A61N 1/32* (2013.01); *C12N 13/00* (2013.01)

(58) Field of Classification Search
CPC .. A61K 41/0023; A61K 31/43; A61K 31/341; A61K 31/496; A61K 31/575; A61K 31/702; A61K 31/4164; A61K 31/5377; A61K 31/7056; A61K 31/7048; A61K 31/7036; A61K 38/14; C12N 13/00
USPC .......................................................... 604/20
See application file for complete search history.

(56) References Cited

U.S. PATENT DOCUMENTS

| | | |
|---|---|---|
| 5,702,359 A | 12/1997 | Hofmann et al. |
| 6,326,177 B1 | 12/2001 | Schoenbach et al. |
| 6,418,341 B1 | 7/2002 | Hofmann et al. |
| 6,669,901 B2 | 12/2003 | Eynard et al. |
| 6,714,816 B1 | 3/2004 | Heller et al. |
| 6,778,853 B1 | 8/2004 | Heller et al. |
| 6,937,890 B2 | 8/2005 | Jaroszeski et al. |
| 7,713,740 B2 | 5/2010 | Jaroszeski et al. |
| 7,769,440 B2 | 8/2010 | Hoff et al. |
| 8,000,813 B2 | 8/2011 | Schoenbach et al. |
| 8,569,027 B2 * | 10/2013 | Ren ........................ C12N 13/00 435/173.1 |
| 8,822,222 B2 | 9/2014 | Beebe et al. |
| 9,238,808 B2 | 1/2016 | Caiafa et al. |
| 2011/0034406 A1 | 2/2011 | Ren et al. |

OTHER PUBLICATIONS

Del Pozo et al, Antimicrobial Agents and Chemotherapy, 2009, 53(1), 35-40.*
Hulsheger et al, Radiat. Environ. Biophys, 1981, 20, 53-65.*
International Search Report and Written Opinion of the International Searching Authority for International Application No. PCT/US2019/017761 dated May 13, 2019.
Fleming, A., "Penicillan", Nobel Lecture, pp. 84-93 (1945).
Kostyanev, T., et al., "The Global Crisis of Antimicrobial Resistance", Antimicrobial Stewardship, Chapter 1, pp. 3-12 (2017).
Aminov, R., "History of antimicrobial drug discovery: Major classes and health impact", Biochemical Pharmacology, vol. 133, pp. 4-19 (2017).
Blaser, M.J., "Missing Microbes. How the Overuse of Antibiotics is Fueling our Modern Plagues", CVJ, vol. 56, p. 1260.
Witte, W., "Medical Consequences of Antibiotic Use in Agriculture", Science, vol. 279, Issue 5353, pp. 996-997 (1998).
"Antibiotic Resistance Threats in the United States, 2013", U.S. Department of Health and Human Services, Centers for Disease Control and Prevention, pp. 1-113 (2013).
David, M.Z. et al., "Recently approved antibacterials for methicillin-resistant *Staphylococcus aureus* (MRSA) and other Gram-positive pathogens: the shock of the new", International Journal of Antimicrobial Agents, vol. 50, pp. 303-307 (2017).

(Continued)

*Primary Examiner* — Ganapathy Krishnan
(74) *Attorney, Agent, or Firm* — Heslin Rothenberg Farley & Mes

(57) ABSTRACT

Provided is a method of reducing a number of viable microbes, including contacting microbes with an antibiotic compound and applying pulses of electricity having a duration of between about 50 nanoseconds and about 900 nanoseconds. The pulses of electricity may have an intensity between about 20 kV/cm and about 40 kV/cm. The pulses of electricity may be applied at a frequency of between about 0.1 Hz and about 10 Hz. The microbes may be a gram-negative or a gram-positive strain of bacteria and the antibiotic may be applied at a concentration for a duration, wherein applying the antibiotic to the strain at the concentration for the duration does not reduce a viable number of bacteria of the strain as much, or at all, when the pulses of electricity are not also applied.

20 Claims, 13 Drawing Sheets

(56) References Cited

OTHER PUBLICATIONS

Mohammad, H., et al., "Repurposing niclosamide for intestinal decolonization of vancomycin-resistant enterococci", International Journal of Antimicrobial Agents, vol. 51, pp. 897-904 (2018).
Thangamani, S., et al., "Repurposing auranofin for the treatment of cutaneous staphylococcal infections", International Journal of Antimicrobial Agents, vol. 47, pp. 195-201 (2016).
Birbir, M., et al., "Inactivation of *Escherichia coli* by alternative electric current in rivers discharged into sea", Journal of Electrostatics, vol. 67, pp. 640-645 (2009).
Amiali, M., et al., "Synergistic effect of temperature and pulsed electric field on inactivation of *Escherichia coli* O157:H7 and *Salmonella enteritidis* in liquid egg yolk", Journal of Food Engineering, vol. 79, pp. 689-694 (2007).
Walkling-Ribeiro, M., et al., "Processing temperature, alcohol and carbonation levels and their impact on pulsed electric fields (PEF) mitigation of selected characteristic microorganisms in beer", Food Research International, vol. 44, pp. 2524-2533 (2011).
Zhang, Q., et al., "Inactivation of *E. coli* for Food Pasteurization by High-Strength Pulsed Electric Fields", Journal of Food Processing and Preservation, vol. 19, pp. 103-118 (1995).
Francolini I., et al., "Prevention and control of biofilm-based medical-device-related infections", FEMS Immunol Med Microbiol, vol. 59, pp. 227-238 (2010).
Del Pozo, J.L., et al., "Effect of Electrical Current on the Activities of Antimicrobial Agents against Pseudomonas aeruginosa, *Staphylococcus aureus*, and *Staphylococcus epidermidis* Biofilms", Antimicrobial Agents and Chemotherapy, vol. 53, No. 1, pp. 35-40 (2009).
Vadlamani, A., et al., "Synergistic bacterial inactivation by combining antibiotics with nanosecond electric pulses", Applied Microbiology and Biotechnology, vol. 102, pp. 7589-7596 (2018).
Perni, S., et al., "Bacterial cells exposed to nanosecond pulsed electric fields show lethal and sublethal effects", International Journal of Food Microbiology, vol. 120, pp. 311-314 (2007).
Weaver, J.C., et al., "Theory of electroporation: A review", Bioelectrochemistry and Bioenergetics, vol. 41, pp. 135-160 (1996).
Nuccitelli R., et al., "Nanosecond pulsed electric fields cause melanomas to self-destruct", Biochemical and Biophysical Research Communications, vol. 343, pp. 351-360 (2006).
Nuccitelli R., et al., "First-in-human trial of nanoelectroablation therapy for basal cell carcinoma: proof of method", Experimental Dermatology, vol. 23, pp. 130-142 (2014).
Del Pozo, J.L., et al., "Bioelectric effect and bacterial biofilms. A systematic review", The International Journal of Artificial Organs, vol. 31, No. 9, pp. 786-795 (2008).
Schoenbach, K.H., et al., "The Effect of Pulsed Electric Fields on Biological Cells: Experiments and Applications", IEEE Transactions of Plasma, Science, vol. 25, No. 2, pp. 284-292 (1997).

National Institutes of Health, National Cancer Institute Term Browser results for Fusidic Acid (Code C65793), retrieved Feb. 1, 2019.
Schoenbach, K.H., et al., "A Scaling Law for Membrane Permeabilization with Nanopulses", IEEE Transactions on Dielectrics and Electrical Insulation, vol. 16, No. 5, pp. 1224-1235 (2009).
Garner, A.L., et al., "Design, characterization and experimental validation of a compact, flexible pulsed power architecture for ex vivo platelet activation", PLOS One, vol. 12, No. 7, e0181214, pp. 1-27 (2017).
Yarmush, M.L., et al., "Electroporation-Based Technologies for Medicine: Principles, Applications, and Challenges", Annual Review Biomedical Engineering, vol. 16, pp. 295-320 (2014).
Khan, S.I., et al., "Eradication of Multidrug-Resistant Pseudomonas Biofilm with Pulsed Electric Fields", Biotechnology and Bioengineering, vol. 113, No. 3, pp. 643-650 (2016).
Frey, W., et al., "Inactivation of Pseudomonas putida by Pulsed Electric Field Treatment: A Study on the Correlation of Treatment Parameters and Inactivation Efficiency in the Short-Pulse Range", J. Membrane Biol., vol. 246, pp. 769-781 (2013).
Guionet, A., et al., "Effect of nanosecond pulsed electric field on *Eschericia coli* in water: inactivation and impact on protein changes", Journal of Applied Microbiology, vol. 117, pp. 721-728 (2014).
Mir, L.M., et al., "Introduction of Definite Amounts of Nonpermeant Molecules into Living Cells after Electropermeabilization: Direct Access to the Cytosol", Experimental Cell Research, vol. 175, pp. 15-25 (1988).
Hulsheger, H., et al., "Killing of Bacteria with Electric Pulses of High Field Strength", Radiation and Environmental Biophysics, vol. 20, pp. 53-65 (1981).
Bockmann, R.A., et al., "Kinetics, Statistics, and Energetics of Lipid Membrane Electroporation Studied by Molecular Dynamics Simulations", Biophysical Journal, vol. 95, pp. 1837-1850 (2008).
Sosa, A., et al., "Antimicrobial Resistance in Developing Countries", Chapter 2 Mechanisms of Antimicrobial Resistance by Byarugaba, D.K., pp. 15-26 (2010).
Miklavcic, D., et al., Electrochemotherapy: from the drawing board into medical practice, vol. 13, No. 29, pp. 1-20 (2014).
Talele, S., et al., "Modelling single cell electroporation with bipolar pulse parameters and dynamic pore radii", Journal of Electrostatics, vol. 68, pp. 261-274 (2010).
Nikolova, B., et al., "Fluorescent Imaging for Assessment of the Effect of Combined Application of Electroporation and Rifampicin on HaCaT Cells as a New Therapeutic Approach for Psoriasis", Sensors, vol. 13, pp. 3625-3634 (2013).
Novickij, V., et al., "Overcoming Antimicrobial Resistance in Bacteria Using Bioactive Magnetic Nanoparticles and Pulsed Electromagnetic Fields", Frontiers in Microbiology, vol. 8, Article 2678, pp. 1-8 (2018).
Uecker, D., et al., "Pulse Biosciences", filed pursuant to Rule 433, Registration Statement 333-208694, Mar. 28, 2016.
Li, X., et al., "The Challenge of Efflux-Mediated Antibiotic Resistance in Gram-Negative Bacteria", Clinical Microbiology Reviews, vol. 28, No. 2, pp. 337-418 (2015).

* cited by examiner

INACTIVATING BACTERIA WITH ELECTRIC PULSES AND ANTIBIOTICS

CROSS-REFERENCE TO RELATED APPLICATIONS

This application is a continuation of International Application No. PCT/US2019/017761, filed on Feb. 13, 2019, and published on Aug. 22, 2019, and claims benefit of priority from U.S. Provisional Patent Application No. 62/630,219, filed Feb. 13, 2018, the entire contents of which applications are incorporated herein by reference.

GOVERNMENT RIGHTS STATEMENT

This invention was made with Government support under grant number NRC-HQ-84-14-G-0048 awarded by the U.S. Nuclear Regulatory Commission. The Government has certain rights in the invention.

FIELD OF THE INVENTION

The subject matter disclosed herein relates to inhibiting bacteria by applying antibiotics thereto in combination with the application of voltage pulses. More specifically, this disclosure relates to applying electric pulses of nanosecond duration in combination with the application of antibiotics, the application of both of which in combination may result in an enhanced inhibition or prevention of bacterial growth, proliferation, or survival.

BACKGROUND OF THE INVENTION

Antimicrobial resistance (AMR) is a major challenge and growing global health crisis, with many scientists and public health professionals sounding the alarm on a "post-antibiotic" era. While the Center for Disease Control (CDC) and WHO have issued statements and guidelines concerning antibiotic use and antibiotic resistant microbes and initiated tracking protocols at medical facilities, this does not fully address the underlying causes for resistance development and emergence. The overuse of antibiotics in agriculture and medicine is a key driver of antibiotic resistance and high production animal farming methods promote the spread of disease in overcrowded spaces. Farmers often apply ineffective levels of antibiotics that improve animal growth rates. However, this allows the bacteria in that environment to more easily develop resistance. In medical settings, antibiotics are often prescribed for non-bacterial infections. Additionally, doctors frequently apply broad spectrum antibiotics rather than identifying the causative organism and applying a targeted treatment due to the lack of rapid, low-cost testing methods. Patients often stop taking medication upon becoming asymptomatic; however, the surviving microorganisms can acquire resistance to subsequent treatments with the same antibiotic.

The increased obsolescence of antibiotics, combined with the slow pace of new antibiotic development, especially in combating carbapenem-resistance in gram negative bacteria, such as *K pneumoniae*, and fluoroquinolone resistance in *P aeruginosa* has forced medical facilities to more frequently treat gram negative infections with older drugs, such as colistin, drugs considered treatments of last resort. Currently, gram-positive infections, such as Methicillin-resistant *Staphylococcus aureus* (MRSA) comprise a significant portion of clinically relevant bacteria, and numerous novel antimicrobial drugs have been licensed to target them in the past decade. While the list of essential medicines includes many drugs for combating gram-positive infections, several of these drugs, such as linezolid and vancomycin, have no clinically significant effect on most gram-negative bacteria.

The scientific and medical communities are currently exploring methods to combat this problem, including the development of new monitoring and diagnostic tools to improve data collection, in vitro systems to mimic evolutionary environments to determine the time between antibiotic susceptibility and resistance, and methods to interfere with existing resistance mechanisms while simultaneously developing new antibiotics. The latter method is one of escalation, since any use of antibiotics in humans or animals will breed resistance in the surviving microbes, which can acquire transmittable genetic material. Subsequent generations of these surviving microbes require higher doses of that antibiotic, ultimately necessitating the development of a new class of antibiotics. While new techniques, such as detecting antimicrobial compounds as they are produced in their natural environment in the soil instead of a Petri dish using electronic chips, will facilitate antibiotic development. However, the traditional life cycle of these drug development methods and clinical use will inevitably result in stronger, more resistant superbugs.

Thus, there remains a need to improve the antibacterial regimen with lower doses of antibiotics to prevent development of resistance and to increase spectrum of bacteria susceptible to treatment with a given antibacterial regimen. The present disclosure is directed to overcoming these and other deficiencies in the art.

SUMMARY OF THE INVENTION

In one aspect, provided is a method of reducing a number of viable microbes, including contacting microbes with an antibiotic compound and applying pulses of electricity having a duration of between about 50 nanoseconds and about 900 nanoseconds. In an embodiment, the pulses of electricity have an intensity and the intensity is between about 20 kV/cm and about 40 kV/cm. For example, the intensity may be about 20 kV/cm, or may be about 30 kV/cm, or may be about 40 kV/cm. In another embodiment, the pulses of electricity are applied at a frequency of between about 0.1 Hz and about 10 Hz.

In yet another embodiment, the microbes are a strain of bacteria and the antibiotic is applied at a concentration for a duration, wherein applying the antibiotic to the strain at the concentration for the duration does not reduce a viable number of bacteria of the strain when the pulses of electricity are not also applied to the strain. In an example, the strain is a gram-negative strain. In another example, the strain is a gram-positive strain.

In another embodiment, the microbes are a strain of bacteria and the antibiotic is applied at a concentration for a duration, wherein the reducing is greater when the antibiotic is applied to the strain at the concentration for the duration when the pulses of electricity are applied to the strain than when the antibiotic is applied to the strain at the concentration for the duration when the pulses of electricity are not applied to the strain. In an example, the strain is a gram-negative strain. In another example, the strain is a gram-positive strain.

In a further embodiment, the microbes are a strain of bacteria, wherein applying the pulses of electricity at the intensity to the strain does not reduce a viable number of bacteria of the strain when the strain is not also contacted with an antibiotic. In an example, the strain is a gram-negative strain. In another example, the strain is a gram-positive strain.

In still another embodiment, the antibiotic is selected from at least one of an aminoglycoside antibiotic, an ansamycin antiobiotic, a beta-lactam antibiotic, a glycopeptide antibiotic, a lincosamide antibiotic, a lipopeptide antibiotic, a macrolide antibiotic, a monobactam antibiotic, a nitrofuran antibiotic, an oxazolidinone antibiotic, a quinolone antibiotic, a fluoroquinolone antibiotic, a sulfonamide antibiotic, a tetracycline antibiotic, pexiganan, fusidic acid, mupirocin, and any combination of at least two of the foregoing. In still a further embodiment, the antibiotic is selected from at least one of tobramycin, streptomycin, rifampicin, vancomycin, clindamycin, daptomycin, erythromycin, linezolid, penicillin, minocycline, pexiganan, fusidic acid, mupirocin, bacitracin, neomycin, polymixin B, metronidazole, silver, zinc, copper, and any combination of at least two of the foregoing.

In yet a further embodiment, the microbe is *Staphylococcus aureus, Staphylococcus epidermidis, Escherichia coli, Acenitobacter baumanii, Klebsiella pneumoniae,* or *Pseudomonas aeruginosa.* In another embodiment, the microbe is vancomycin-resistant *Staphylococcus aureus*, methicillin-resistant *Staphylococcus aureus*, a strain of multidrug-resistant *Pseudomonas aeruginosa*, or a strain of multidrug-resistant *Escherichia coli.*

In a further embodiment, contacting further includes administering the antibiotic to a human, and applying further includes applying the electric pulses to the human. In an example, administering is selected from administering topically and administering systemically.

In another aspect, provided is a method of reducing a number of viable microbes, including contacting microbes with an antibiotic compound and applying pulses of electricity having a duration of between about 50 nanoseconds and about 900 nanoseconds, wherein the pulses of electricity have an intensity and the intensity is between about 20 kV/cm and about 40 kV/cm. For example, the intensity may be about 20 kV/cm, or may be about 30 kV/cm, or may be about 40 kV/cm. In another embodiment, the pulses of electricity are applied at a frequency of between about 0.1 Hz and about 10 Hz.

In yet another embodiment, the microbes are a strain of bacteria and the antibiotic is applied at a concentration for a duration, wherein applying the antibiotic to the strain at the concentration for the duration does not reduce a viable number of bacteria of the strain when the pulses of electricity are not also applied to the strain. In an example, the strain is a gram-negative strain. In another example, the strain is a gram-positive strain.

In still another embodiment, the microbes are a strain of bacteria and the antibiotic is applied at a concentration for a duration, wherein the reducing is greater when the antibiotic is applied to the strain at the concentration for the duration when the pulses of electricity are applied to the strain than when the antibiotic is applied to the strain at the concentration for the duration when the pulses of electricity are not applied to the strain. In an example, the strain is a gram-negative strain. In another example, the strain is a gram-positive strain.

In a further embodiment, the microbes are a strain of bacteria, wherein applying the pulses of electricity at the intensity to the strain does not reduce a viable number of bacteria of the strain when the strain is not also contacted with an antibiotic. In an example, the strain is a gram-negative strain. In another example, the strain is a gram-positive strain.

In still another embodiment, the antibiotic is selected from at least one of an aminoglycoside antibiotic, an ansamycin antiobiotic, a beta-lactam antibiotic, a glycopeptide antibiotic, a lincosamide antibiotic, a lipopeptide antibiotic, a macrolide antibiotic, a monobactam antibiotic, a nitrofuran antibiotic, an oxazolidinone antibiotic, a quinolone antibiotic, a fluoroquinolone antibiotic, a sulfonamide antibiotic, a tetracycline antibiotic, pexiganan, fusidic acid, mupirocin, and any combination of at least two of the foregoing. In still a further embodiment, the antibiotic is selected from at least one of tobramycin, streptomycin, rifampicin, vancomycin, clindamycin, daptomycin, erythromycin, linezolid, penicillin, minocycline, pexiganan, fusidic acid, mupirocin, bacitracin, neomycin, polymixin B, metronidazole, silver, zinc, copper, and any combination of at least two of the foregoing.

In yet a further embodiment, the microbe is *Staphylococcus aureus, Staphylococcus epidermidis, Escherichia coli, Acenitobacter baumanii, Klebsiella pneumoniae,* or *Pseudomonas aeruginosa.* In another embodiment, the microbe is vancomycin-resistant *Staphylococcus aureus*, methicillin-resistant *Staphylococcus aureus*, a strain of multidrug-resistant *Pseudomonas aeruginosa*, or a strain of multidrug-resistant *Escherichia coli.*

In a further embodiment, contacting further includes administering the antibiotic to a human, and applying further includes applying the electric pulses to the human. In an example, administering is selected from administering topically and administering systemically.

In yet another aspect, provided is a method of reducing a number of viable microbes, including contacting microbes with an antibiotic compound and applying pulses of electricity having a duration of between about 50 nanoseconds and about 900 nanoseconds. In an embodiment, the pulses of electricity have an intensity and the intensity is between about 20 kV/cm and about 40 kV/cm. In an example, the intensity is about 20 kV/cm. In another example, the intensity is about 30 kV/cm. In yet another example, the intensity is about 40 kV/cm. In another embodiment, the pulses of electricity are applied at a frequency of between about 0.1 Hz and about 10 Hz.

In an example, the antibiotic includes an aminoglycan. In another example, the antibiotic includes tobramycin. In yet another example, the antibiotic includes an ansamycin. In still another example, the antibiotic comprises rifampicin.

In a further example, the microbe includes a strain of *Staphylococcus aureus.* In yet a further example, the microbe includes a strain of *Esherichia coli.* In still a further example, the antibiotic includes a glycopeptide.

In another example, the antibiotic includes vancomycin. In yet another example, the antibiotic includes an oxazolidinone. In still another example, the antibiotic includes linezolid. In a further example, the antibiotic includes an ansamycin. In yet a further example, the antibiotic includes rifampicin. In still a further example, the antibiotic includes mupirocin. In an example, the antibiotic includes a macrolide. In another example, the antibiotic includes erythromycin. In yet another example, the antibiotic includes fusidic acid.

In another example, the microbe com includes prises a multidrug-resistant strain of *Escherichia coli.* In yet another example, the microbe includes *Klebsiella pneumoniae.* In still another example, the microbe includes a multidrug-resistant strain of *Pseudomonas aeruginosa.*

In a further example, the microbes are a strain of bacteria, wherein applying the pulses of electricity at the intensity to the strain does not reduce a viable number of bacteria of the strain when the strain is not also contacted with an antibiotic. In an example, the strain is a gram-negative strain. In another example, the strain is a gram-positive strain.

In still a further example, contacting further includes administering the antibiotic to a human, and applying further includes applying the electric pulses to the human. In yet another example, administering is selected from administering topically and administering systemically.

BRIEF DESCRIPTION OF THE DRAWINGS

These and other features, aspects, and advantages of the present disclosure will become better understood when the following detailed description is read with reference to the accompanying drawings, wherein:

FIG. 8A Combining EPs at either electric field enhances MRSA inactivation compared drug alone with the 30 kV/cm EPs inducing greater inactivation for both concentrations of all drugs.

FIG. 8B. Synergy induced by combining EPs with antibiotics (0-log indicates no synergy). Combining the 20 kV/cm EP with 2 µg/mL rifampicin induced a statistically significant synergistic inactivation compared to the same concentration of other antibiotics studied.

FIG. 9A. Applying the 30 kV/cm EPs induces over a 3-log reduction in K. pneumoniae and combining EPs with 2 µg/mL or 20 µg/mL of mupirocin, rifampicin, vancomycin results in statistically significant increases in bacteria inactivation from 4-log to 5-log. FIG. 9B. Synergy induced by combining EPs with antibiotics (0-log indicates no synergy). Combining 2 µg/mL or 20 µg/mL of mupirocin, rifampicin, or vancomycin with the 30 kV/cm EPs induced at least approximately 1-log synergy.

FIG. 10A Applying 20 kV/cm EPs induces approximately 1-log reduction and combining the 20 kV/cm EPs with either 2 µg/mL or 20 µg/mL of any of the antibiotics induces approximately 2-log to 3-log reduction, which is statistically significant for the 2 µg/mL doses. Applying the 30 kV/cm EPs induces approximately a 3-log reduction in E. coli and combining these EPs with 2 µg/mL or 20 µg/mL of any of the antibiotics induces statistically significant reductions of 3-log to 5-log and 3-log to 6-log, respectively. FIG. 10B Synergy induced by combining EPs with antibiotics (0-log indicates no synergy). Adding 2 µg/mL of any drug except for vancomycin to the 20 kV/cm EPs induced at least 1-log of statistically significant synergy. Adding 20 µg/mL of linezolid and rifampicin induced approximately 2-log of statistically significant synergy. Combining 2 µg/mL or 20 µg/mL of any of the drugs considered with the 30 kV/cm EPs induced at least 1-log synergy.

FIG. 11A Applying 20 kV/cm EPs induces approximately 1-log reduction and combining the 20 kV/cm EPs with either 2 µg/mL or 20 µg/mL of any of the antibiotics induces approximately 2-log to 3-log reduction, which is statistically significant for the 2 ☐g/mL doses. Applying the 30 kV/cm EPs induces approximately a 3-log reduction in E. coli and combining these EPs with 2 µg/mL or 20 µg/mL of any of the antibiotics induces statistically significant reductions of 3-log to 5-log and 3-log to 6-log, respectively. FIG. 11B Synergy induced by combining EPs with antibiotics (0-log indicates no synergy). Adding 2 µg/mL of any drug except for Van to the 20 kV/cm EPs induced at least 1-log of statistically significant synergy. Adding 20 µg/mL of linezolid and rifampicin induced approximately 2-log of statistically significant synergy.

Figure 1:
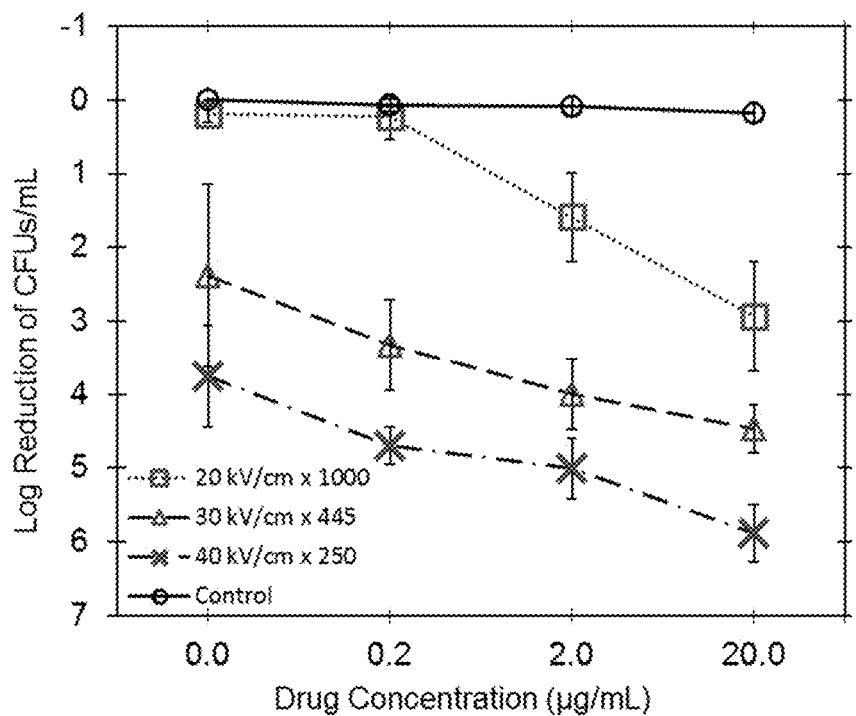
FIG. 1 shows effects of combining trains of 300 ns electric pulses with the same energy, but different electric fields and number of pulses, with different concentrations of the tobramycin synergistically reduced an amount of viable S. aureus.

Combining 2 µg/mL or 20 µg/mL of any of the drugs considered with the 30 kV/cm EPs induced at least 1-log synergy.

DETAILED DESCRIPTION OF THE INVENTION

This disclosure relates to a method of reducing a number of viable microbes. A method may include contacting microbes with an antibiotic and applying electric pulses of a duration on the order of nanoseconds. In an aspect, combining an application of electric pulses of a duration on the order of nanoseconds enhances an antibacterial effect of one or more antibiotics. Thus, in an example, contacting a given strain of microbe with a given concentration of a given antibiotic may not result in an antimicrobial effect on the microbe in the absence of coadministration of electric pulses of nanosecond duration, but when combined with such electric pulses such antibiotic may have an antibiotic effect.

Electric pulses (EPs) are known to be able to eradicate microorganisms, such as by inducing lysis. Application of EPs has also been employed for some medical and biological applications, including extending food shelf life, permeabilizing cells to facilitate gene and molecular delivery, permeabilizing tumors to enhance the delivery of chemotherapeutics, and directly killing tumors through irreversible electroporation. Such applications typically involve direct EP targeting of cell membranes using electric fields of hundreds of V/cm to a few kV/cm with durations from microseconds to milliseconds.

Technology development over the past two decades has led to the biomedical application of nanosecond-duration EPs (NSEPs) (such as EPs with a duration of between about 1 nanosecond and about 1 microsecond) with field strengths ranging from tens of kV/cm to a few hundred kV/cm. These shorter durations enable charging intracellular membranes prior to the cell membrane, permitting intracellular manipulation with minimal cell membrane impact. Without being limited to any particular theory of activity, NSEPs may also permit creating membrane nanopores that enable ions and small molecules to enter the cell while prohibiting larger molecules.

Provided in the present disclosure is a method for reducing drug dose and EP energy input which may reduce numbers of viable microbes, including gram-positive and gram-negative bacteria. For example, combining application of electric pulses of nanosecond duration over a relatively brief time frame (e.g., anywhere from about one minute to about one hour) may enhance an ability of an antibiotic, applied with or without one or more additional antibiotics, to reduce viability of microbes to which such treatment is applied. An abbreviated time during which NSEPs may be applied in order to so inhibit viability of microbes in the presence of antibiotics, including enhancing antimicrobial effectiveness of a concentration of antibiotics applied, may advantageously facilitate treatment. For example, NSEPs could be applied to a subject (e.g., human or animal) over a period of an hour or less (or 30 minutes or less or 20 minutes or less or 15 minutes or less or 10 minutes or less of 5 minutes of less or two minutes or less) while antibiotics are applied (e.g., topically near a site where NSEPs are applied or systemically such as through any systemic administration route appropriate for a given antibacterial drug). Because administration of NSEPs over a period of more than one hour may be more difficult to accomplish, a method disclosed herein including administration of NSEPs for one hour or less provides significant advantages over alternatives. In other examples, NSEPs may be administered across a duration of time in excess of an hour. For example, NSEPs may be administered for two, three four, five, six, seven, eight, nine, ten, eleven, twelve, or more hours.

EPs may be administered according to various parameters. Such parameters include intensity of EP applied, duration of EP, frequency of EP administration, number of EPs applied in a train of EPs, number of trains of EPs applied, and duration of time between trains of EPs.

As to intensity of EPs, as disclosed herein, EPs may be within a range of about 20 kV/cm to about 40 kV/cm. In this case, "about" means intensity of EPs may vary somewhat from these precise values while still falling within the intensities as so described. For example, "about" may mean within +/−5% of a value. Intensity may be within such range, or within a sub-range thereof. For example, intensity of an EP as disclosed herein may be about 20 kV/cm, about 25 kV/cm, about 30 kV/cm, about 35 kV/cm, or about 40 kV/cm Alternatively, EPs may be within a range from about 15 kV/cm to about 25 kV/cm, from about 20 kV/cm to about 30 kV/cm, from about 25 kV/cm to about 30 kV/cm, from about 25 kV/cm to about 35 kV/cm, from about 30 kV/cm to about 35 kV/cm, from about 30 kV/cm to about 40 kV/cm, or from about 35 kV/cm to about 40 kV/cm, or within any subranges within these ranges. In other examples, EPs may have an intensity below about 20 kV/cm. For example, an EP may have an intensity of about 15 kV/cm, or about 10 kV/cm, or about 5 kV/cm, or about 1 kV/cm, or any value therebetween. In other examples, an EP may have an intensity above about 40 kV/cm. For example, an EP may have an intensity of about 45 kV/cm, or about 50 kV/cm, or about 55 kV/cm, or about 60 kV/cm, or about 70 kV/cm, or about 75 kV/cm, or about 80 kV/cm, or about 85 kV/cm, or about 90 kV/cm, or about 100 kV/cm, or any value or range therebetween.

As to duration of EP, EPs may be nanosecond-EPs (NSEPs), in that they may have a duration of between about 1 ns and about 1 microsecond. In this case, "about" means duration of EPs may vary somewhat from these precise values while still falling within the intensities as so described. For example, "about" may mean within +/−5% of a value. For example, NSEPs may be a duration of between about 50 ns and about 900 ns, or any value or range therebetween. For example, an NSEP may have a duration of about 50 ns, or about 60 ns, 70 ns, or about 80 ns, or about 90 ns, or about 100 ns, or about 110 ns, or about 120 ns, or about 130 ns, or about 140 ns, or about 150 ns, or about 160 ns, or about 170 ns, or about 180 ns, or about 190 ns, or about 200 ns, or about 210 ns, or about 220 ns, or about 230 ns, or about 240 ns, or about 250 ns, or about 260 ns, or about 270 ns, or about 280 ns, or about 290 ns, or about 300 ns, or about 310 ns, or about 320 ns, or about 330 ns, or about 340 ns, or about 350 ns, or about 360 ns, or about 370 ns, or about 380 ns, or about 390 ns, or about 400 ns, or about 410 ns, or about 420 ns, or about 430 ns, or about 440 ns, or about 450 ns, or about 460 ns, or about 470 ns, or about 480 ns, or about 490 ns, or about 500 ns, or about 510 ns, or about 520 ns, or about 530 ns, or about 540 ns, or about 550 ns, or about 560 ns, or about 570 ns, or about 580 ns, or about 590 ns, or about 600 ns, or about 610 ns, or about 620 ns, or about 630 ns, or about 640 ns, or about 650 ns, or about 660 ns, or about 670 ns, or about 680 ns, or about 690 ns, or about 700 ns, or about 710 ns, or about 720 ns, or about 730 ns, or about 740 ns, or about 750 ns, or about 760 ns, or about 770 ns, or about 780 ns, or about 790 ns, or about 800 ns, or about 810 ns, or about 820 ns, or about 830 ns, or about 840 ns, or about 850 ns, or about 860 ns, or about 870 ns, or about 880 ns, or about 890 ns, or about 900 ns.

An NSEP may also have a duration within any subrange within about 50 ns to about 900 ns. For example, an NSEP may have a duration of between about 50 ns and 100 ns, about 100 ns and about 150 ns, about 150 ns and about 200 ns, about 250 ns and about 300 ns, about 300 ns and about 350 ns, about 350 ns and about 400 ns, about 400 ns and about 450 ns, about 450 ns and about 500 ns, about 500 ns and about 550 ns, about 550 ns and about 600 ns, about 600 ns and about 650 ns, about 650 ns and about 700 ns, about 700 ns and about 750 ns, about 750 ns and about 800 ns, about 800 ns and about 850 ns, about 850 ns and about 900 ns, about 100 ns and about 200 ns, about 200 ns and about 300 ns, about 300 ns and about 400 ns, about 400 ns and about 500 ns, about 500 ns and about 600 ns, about 600 ns and about 700 ns, about 700 ns and about 800 ns, about 800 ns and about 900 ns, about 100 ns and about 300 ns, about 300 ns and about 500 ns, about 500 ns and about 700 ns, about 700 ns and about 900 ns, about 100 ns and about 500 ns, or about 500 ns and about 900 ns.

In some examples, NSEPs may have a duration of less than about 50 ns. For example, an NSEP may have a duration of about 45 ns, about 40 ns, about 35 ns, about 30 ns, about 25 ns, about 20 ns, about 15 ns, about 10 ns, about 5 ns, or about 1 ns, or a duration within a range therebetween. In other examples, NSEPs may have a duration of longer than about 900 ns, such as about 910 ns, about 920 ns, about 930 ns, about 940 ns, about 950 ns, about 960 ns, about 970 ns, about 980 ns, about 990 ns, about 995 ns, or about 999 ns. NSEPs have a duration of less than 1 μs.

In some circumstances, EP of durations of 1 μs or higher may disadvantageously impair functioning or viability or non-microbial cells. For example, where EPs are administered to a subject such as a human subject along with application or administration of an antibacterial or other antimicrobial substance for the purpose of reducing a number of viable microbes, applying EP with a duration of 1 μs or longer may disadvantageous also damage cells and/or tissue of the subject not just decrease viability of microbes. Thus, application of NSEPs as disclosed herein explicitly excludes application of EPs with a duration of 1 μs or longer. Surprisingly, as disclosed herein, applying NSEPs over an abbreviated time frame produces a substantial reduction in microbe viability when paired with administration of one or more antimicrobial agents, including when neither the EP alone or concentration of antimicrobial agent alone has an effect of reducing a number of viable microbes or effects a lesser reduction of a number of viable microbes than does application of either EP or antimicrobial agent alone. Such an effect is found without application of EPs of a duration of 1 μs or longer, thereby enhancing an antimicrobial effect which minimizing, reducing, eliminating, or avoiding deleterious effects on cells or tissue of a subject such as a human subject receiving such treatment.

In other examples, such as when a severe infection may occur or be present, one or more EP of longer then about 1 μs may be administered even at the risk of damaging tissue beyond eradicating microbes. For example, some damage to tissue may be an acceptable trade-off for reducing a number of viable microbes. Some tissue may be lost during debridement procedure that may be provided either before or after the application of NSEP and an antimicrobial composition.

EPs may be administered in a series or train of EPs, meaning more than one NSEP applied in temporally proximate succession. For example, anywhere from 2 to 200 NSEPs may be applied in a train with a frequency of administration of between about 0.1 Hz and about 10 Hz. In this case, "about" means frequency of EPs may vary somewhat from these precise values while still falling within the intensities as so described. For example, 2, about 5, about 10, about 12, about 15, about 17, about 20, about 22, about 25, about 27, about 30, about 32, about 35, about 37, about 40, about 42, about 45, about 47, about 50, about 52, about 55, about 57, about 60, about 62, about 65, about 67, about 70, about 72, about 75, about 77, about 80, about 82, about 85, about 87, about 90, about 92, about 95, about 97, about 100, about 102, about 105, about 107, about 110, about 112, about 15, about 117, about 120, about 122, about 125, about 127, about 130, about 132, about 135, about 137, about 140, about 142, about 145, about 147, about 150, about 152, about 155, about 157, about 160, about 162, about 165, about 167, about 170, about 172, about 175, about 177, about 180, about 182, about 185, about 187, about 190, about 192, about 195, about 197, or about 200 EPs may be administered in a train of between 0.1 Hz to about 10 Hz. In this case, "about" means the number of EPs may be within +/−2 of the number indicated. Any number of NSEPs or subrange within the foregoing identified number of NSEPs may also be applied. In an example, between about 15 and about 20, about 10 and about 40, or about 20 and about 100 NSEPs may be administered at a frequency of between about 0.1 Hz and about 10 Hz.

In another example, anywhere from 2 to 1,000 NSEP applied in temporally proximate succession. For example, anywhere from 2 to 1,000 NSEPs may be applied in a train with a frequency of administration of between about 0.1 Hz and about 10 Hz. In this case, "about" means frequency of EPs may vary somewhat from these precise values while still falling within the intensities as so described. For example, 2, about 10, about 50, about 100, about 150, about 200, about 250, about 300, about 350, about 400, about 450, about 500, about 550, about 600, about 650, about 700, about 750, about 800, about 850, about 900, about 950, about 1,000, about 1,050, about 1,100, about 1,150, about 1,200, about 1,250, about 1,300, about 1,350, about 1,400, about 1,450, about 1,500, about 1,550, about 1,600, about 1,650, about 1,700, about 1,750, about 1,800, about 1,850, about 1,900, about 1,950, about 2,000, about 2,050, about 2,150, about 2,100, about 2,150, about 2,200, about 2,250, about 2,300, about 2,350, about 2,400, about 2,450, about 2,500, about 2,550, about 2,600, about 2,650, about 2,700, about 2,750, about 2,800, about 2,850, about 2,900, about 2,950, about 2,300, about 2,350, about 2,400, about 2,450, about 2,500, about 2,550, about 2,600, about 2,650, about 2,700, about 2,750, about 2,800, about 2,850, about 2,900, about 2,950, or about 3,000 EPs may be administered in a train of between 0.1 Hz to about 10 Hz. In this case, "about" means the number of EPs may be within +/−25 of the number indicated. In another example, more than about 3,000 NSEPs may be administered (such as bout 4,000 or about 5,000 or more). Any number of NSEPs or subrange within the foregoing identified number of NSEPs may also be applied. In an example, between about 100 and about 500, about 400 and about 800, or about 600 and about 1,000 NSEPs may be administered at a frequency of between about 0.1 Hz and about 10 Hz.

In some circumstances, EPs numbering in the hundreds or 1,000 or more at a frequency of between about 0.1 Hz and about 10 Hz may disadvantageously impair functioning or viability or non-microbial cells, particularly at higher intensities (for example, above about 20 kV/cm). For example, where EPs are administered to a subject such as a human subject along with application or administration of an antibacterial or other antimicrobial substance for the purpose of reducing a number of viable microbes, applying EPs numbering in the hundreds or 1,000 or more at a frequency of between about 0.1 Hz and about 10 Hz at higher intensities may disadvantageous also damage cells and/or tissue of the subject not just decrease viability of microbes. Surprisingly, as disclosed herein, applying NSEPs over an abbreviated time frame produces a substantial reduction in microbe viability when paired with administration of one or more antimicrobial agents, including when neither the EP alone or concentration of antimicrobial agent alone has an effect of reducing a number of viable microbes or effects a lesser reduction of a number of viable microbes than does application of either EP or antimicrobial agent alone. Such an effect is found without application of EPs numbering in the hundreds or 1,000 or more at a frequency of between about 0.1 Hz and about 10 Hz, thereby enhancing an antimicrobial effect which minimizing, reducing, eliminating, or avoiding deleterious effects on cells or tissue of a subject such as a human subject receiving such treatment.

In other examples, such as when a severe infection may occur or be present, one or more EPs numbering in the hundreds or 1,000 or more at a frequency of between about 0.1 Hz and about 10 Hz may be administered even at the risk of damaging tissue beyond eradicating microbes. For example, some damage to tissue may be an acceptable trade-off for reducing a number of viable microbes. Some tissue may be lost during debridement procedure that may be provided either before or after the application of NSEP and an antimicrobial composition.

Frequency of administration of NSEPs within a train may be as low as about 0.1 Hz or as high as about 10 Hz. In an example, frequency is about 1 Hz. In another example, frequency is between about 0.5 Hz and about 2 Hz. In another example, frequency may be about 0.5 Hz, about 1.0 Hz, about 1.5 Hz, about 2.0 Hz, about 2.5 Hz, about 3.0 Hz, about 3.5 Hz, about 4.0 Hz, about 4.5 Hz, about 5.0 Hz, about 5.5 Hz, about 6.0 Hz, about 6.5 Hz, about 7.0 Hz, about 7.5 Hz, about 8.0 Hz, about 8.5 Hz, about 9.0 Hz, about 9.5 Hz, or about 10 Hz. Trains of pulses may also be administered within a range of pulses overlapping these frequencies. For example, a train of NSEPs may be administered at a frequency of between about 1 Hz and about 2 Hz, about 1 Hz and about 3 Hz, about 1 Hz and about 5 Hz, about 3 Hz and about 5 Hz, about 5 Hz and about 7.5 Hz, and about 5 Hz and about 10 Hz.

In some examples, NSEPs may have a duration of between about 50 ns and about 900 ns, may have an intensity of between about 10 kV/cm and about 50 kV/cm, and be administered at between about 0.5 Hz and about 1.5 Hz in a train of between 10 to 20 NSEPs administered. However, explicitly included within the present disclosure is different combinations of the foregoing parameters. Any herein disclosed duration of NSEPs having an intensity of between about 10 kV/cm and about 50 kV/cm, and be administered at between about 0.5 Hz and about 1.5 Hz in a train of between 10 to 20 NSEPs administered, is explicitly included within the present disclosure. Any herein disclosed frequency of NSEP of between about 50 ns and about 900 ns may be administered at between about 0.5 Hz and about 1.5 Hz in a train of between 10 to 20 NSEPs administered, is explicitly included within the present disclosure. Any herein disclosed frequency of NSEPs administered in a train of NSEPs with intensity of between about 10 kV/cm and about 50 kV/cm disclosed frequency of NSEP of between about 50 ns and about 900 ns may be administered in a train of between 10 to 20 NSEPs administered, is explicitly included within the present disclosure. Administration of any number of NSEPs within a train as disclosed herein having a duration of between about 50 ns and about 900 ns, an intensity of between about 10 kV/cm and about 50 kV/cm, and administered at between about 0.5 Hz and about 1.5 Hz, is explicitly included within the present disclosure.

NSEPs may be generated by a Blumlein circuit, which can be built in numerous configurations using capacitors (based on capacitance/charge storage devices), including, but not limited to, ceramic based capacitors, transmission lines, and other dielectrics (such as water). One can control the EP duration by the Blumlein circuit design either by controlling the capacitance or length of the transmission line. Similarly, one can control the pulse shape by modifying the number and nature of the switches to vary the rise- and fall-times, which influences whether the pulse appears square or trapezoidal with respect to time. Increasing the voltage beyond the physical capabilities of the materials used in the Blumlein circuit can be achieved by using a Marx generator, which is a voltage adding device. Typical Marx approaches charge parallel full-bridge switch-capacitor cells at a lower voltage, and through controllable switches, connect in series with a biological sample and discharge into the load at a higher voltage as a function of the number of series components. The resulting series equivalent capacitor (Ceq) voltage is discharged into the biological load, which is calculated as $V_{load} \approx NV_C$ where N is the number of Marx stages with capacitors charged to $V_C$ and depends on stray system capacitance and inductance. Garner, et al. outline various pulse generator designs that may be relevant, including a modular, controllable Marx-based technology developed in collaboration with GE particularly for platelet activation. See A. L. Garner, A. Caiafa, Y. Jiang, S. Klopman, C. Morton, A. S. Torres, A. M. Loveless, and V. B. Neculaes, "Design, Characterization and Experimental Validation of a Compact, Flexible Pulsed Power Architecture for Ex Vivo Platelet Activation," PLOS ONE, 12(7), e0181214 (2017) and A. Caiafa, V. B. Neculaes, A. S. Tones, and A. L. Garner, "Modular Adjustable Pulse Generator," U.S. Pat. No. 9,238,808 B2 (issued 19 Jan. 2016).

In an example, more than one train of NSEPs may be administered. For example, two, three, four, five, six, or more trains may be administered. A duration between trains may be anywhere from between one minute to about one hour. In some examples, the duration between trains may be 5 min, 10 min, 15 min, 20 min, 25 min, 30 min, 35 min, 40 min, 45 min, 50 min, 55 min, or 60 min. In an example, administering more than one train of NSEPs within a duration between trains of 60 min or less, such as 30 min or less or 20 min or less of 15 min or less or 10 min or less or 5 min or less, may advantageously enhance an antimicrobial effect of a method as disclosed herein (surprisingly given the rapidity of effectiveness) by application of more than one train of NSEPs but within an abbreviated time frame for greater ease and improved logistics of application. Thus, treatment times on the order of minutes in accordance with the present disclosure may replace what conventional antimicrobial therapy may require hours or days to attain. In other examples, longer durations between trains may be used when desirable or advantageous or where shorted inter-train intervals are not required or desired. In an example, trains may be separated by about 15 min or 20 min. And of the durations of inter-train intervals as disclosed herein may be about or approximately of the durations identified, in that they may be +/−5% of the duration indicated.

A microbe may be any organism the presence or growth or proliferation of which may be undesirable. For example, a microbe may be a bacteria strain, such as infectious bacteria. A bacteria strain may be gram-positive or gram-negative. Some non-limiting examples of bacteria include *Staphylococcus aureus, Staphylococcus epidermidis, Escherichia coli, Acenitobacter baumanii, Klebsiella pneumoniae,* and *Pseudomonas aeruginosa*. Other bacteria related to any of the foregoing species and different strains thereof may also be included in a method as disclosed herein. On the basis of the present disclosure, it would be understood that a method of reducing a number of viable microbes hereby provided could be applied to numerous different microbes in addition to these examples. Some specific examples include strains of microbes known to be resistant or show low levels of susceptibility to treatment with known antibiotics. Examples include vancomycin-resistant *Staphylococcus aureus*, methicillin-resistant *Staphylococcus aureus*, a strain of multidrug-resistant *Pseudomonas aeruginosa*, or a strain of multidrug-resistant *Escherichia coli*. Some non-limiting examples of strains of bacteria that are known to be resistant or refractory to treatment with one or more antibiotics which are generally effective against other strains of said bacteria include: carbapenem-resistant *Escherichia coli; Klebsiella pneumoniae*; gentamicin, streptomycin and sulfonamide resistant *Pseudomonas aeruginosa*; and methicillin resistant *Staphylococcus aureus* which in some examples may also be resistant to erythromycin and tetracycline. Such strains show low or no susceptibility to exposure to various antibiotics that are otherwise bactericidal and/or bacteriostatic to other strains or other bacteria at comparable concentrations.

In some cases, gram-negative bacteria may be resistant to treatment with an antibiotic that is bacteriostatic or bactericidal as against a gram-positive bacteria. Differences in susceptibility between gram-positive and gram-negative bacteria to a given antibiotic are known and believed attributable to differences between the bacteria in the thicknesses of peptidylglycan layers in cell walls. Thus, a variety of antibiotics may be available for having a bactericidal and/or bacteriostatis effect against gram-positive bacteria because of susceptibility of or because of cell wall peptidylglycan in gram-positive bacteria to certain antibiotics, whereas different peptiglycan cell wall layers in gram-negative may correspond to their lack of susceptibility to the same antibiotics. Certain gram-negative bacteria in particular are known to show high resistance to treatment with certain or broad classes of antibiotics. Surprisingly and advantageously, as provided herein, disclosed is a method for rendering bacteria susceptible to treatment with a given antibiotic when applied in the presence of NSEPs as disclosed herein whereas susceptibility is absent following treatment with the antibiotic in the absence of NSEPs. In other examples, the effectiveness of a dose of an antibiotic may be enhanced by co-administration with NSEPs such that a lower dose or concentration than would otherwise be effective or necessary becomes effective when paired with NSEPs.

Antibiotics of any of a number of difference classes or types may be used in accordance with the method disclosed herein. Examples include aminoglycosides, ansamycins, carbapenems, cephalosporins, antibiotic glycopeptides, lincosamides, abitbiotic lipopeptides, macrolides, monobactams, nitrofurans, oxazolidinones, penicillins, quinolones, fluoroquinolones, sulfonamides, tetracyclines, or others. Any antibiotic from any of these categories may be used in accordance with aspects of the present disclosure. Non-limiting specific examples include, tobramycin, streptomycin, rifampicin, vancomycin, clindamycin, daptomycin, erythromycin, linezolid, penicillin, minocycline, pexiganan, fusidic acid, mupirocin, bacitracin, neomycin, polymixin B, and metronidazole. Other examples include metals or metal ions known to have antimicrobial or antibacterial effects, such as silver, copper, or zinc. In some examples, combinations of any two or more of the foregoing antibiotics or substances with antibiotic activity may be administered concurrently in accordance with an aspect of the present disclosure. In some examples, any one or more of the foregoing may also be explicitly excluded from use in accordance with an aspect of the present disclosure.

Other infectious or other microbes may also be included and rendered susceptible to treatment with NSEPs in combination with application of an antimicrobial agent (whereas susceptibility was absent upon treatment with only the antimicrobial or only the NSEPs, or susceptibility is enhanced upon combined administration of both compared to administration of either alone). For example, a microbe may be a fungus, such as *Candida albicans, Candida auris,* or species of *Aspergillis*. Various antifungal compounds may also be administered in accordance with an aspect of the present disclosure. Non-limiting examples include clotrimazole, econazole, miconazole, terbinafine, fluconazole, ketoconazole, and amphotericin, or other compounds known to have antifungal activities. In some examples, combinations of any two or more of the foregoing antifungals or substances with antifungal activity may be administered concurrently in accordance with an aspect of the present disclosure. In some examples, any one or more of the foregoing antifungals or substances with antifungal activity may also be explicitly excluded from use in accordance with an aspect of the present disclosure. In some other examples, one or more of the foregoing antibiotics or substances with antibiotic activity may be used in combination with any one or more of the foregoing antifungals or substances with antifungal activity in accordance with an aspect of the present disclosure.

In an aspect, inhibiting the growth, proliferation, viability, reproduction, infectivity, or number of microbes may be desirable. As used herein, reducing a number of viable microbes includes any of the foregoing effects on microbe colonies or populations. Included are bacteriostatic and bactericidal effects. An antimicrobial composition may be administered with application of NSEPs in accordance with the present disclosure with the result of inhibiting the growth, proliferation, viability, reproduction, infectivity, or number of microbes present, each and all of which are included in reducing a number of viable microbes. A reduction in a number of viable microbes may result from a strictly bactericidal effect, a bacteriostatic effect, or a combination of the two.

A reduction in a number of viable microbes may be identified by any of a number of known methods. For example, a treatment may be applied to one of two otherwise identical samples, then the samples cultured to measure microbial growth following said treatment as compared to following absence of said treatment. If fewer microbes are present after culturing the sample to which said treatment had been applied relative to the untreated sample, the treatment reduced a number of viable microbes. A sample may be any surface, composition, liquid, substance, surface, tissue, or other material to which treatment as disclosed herein may be applied. In an example, applying NSEPs and an antimicrobial composition to a subject, such as a human or non-human animal subject, results in less infection (less in severity, less in duration, or both, or absence of infection)

than results under similar circumstances, or than would have resulted, without treatment. For example, application of such treatment may slow growth of infectious microbes or otherwise render them more susceptible to a subject's immune system. Such examples of reduced infection are examples of reducing a number of viable microbes.

In some examples, a treatment as disclosed herein may slow or prevent proliferation of microbes and thereby hasten a reduction in number of viable microbes (e.g., increase susceptibility to a subject's immune system). In other examples, a treatment as disclosed herein may kill microbes without immediately eliminating or removing them. Both are examples of a treatment reducing a number of viable microbes.

In other examples, a reduction in a viable number of microbes might not result in a reduced duration, degree, or severity of an infection but may be evinced by culturing a sample and ascertaining an amount of microbial growth supported by such sample (following treatment as opposed to absent treatment). Other measures of a number of viable microbes may be used as well, such as quantitative measures of microbial markers (antigens, genetic material, etc.) present in a sample, or microscopic or other known detection method. In some examples, such reduction of a number of viable microbes may be evident within about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 25 hr, about 26 hr, about 27 hr, about 28 hr, about 29, hr, about 30 hr, about 31 hr, about 32 hr, about 33 hr, about 34 hr, about 35 hr, about 36 hr, about 37 hr, about 38 hr, about 39 hr, about 40 hr, about 41 hr, about 42 hr, about 43 hr, about 44 hr, about 45 hr, about 46 hr, about 47 hr, about 48 hr, about 54 hr, about 60 hr, about 66 hr, about 72 hr, about 78 hr, about 84 hr, about 90 hr, about 96 hr, about 4.5 days, about 5 days, about 5.5 days, about 6 days, about 6.5 days, about 7 days, about 10 days, about 14 days, about 17 days, about 21 days, or about 28 days after administration of electric pulses commenced. In this case, "about" means within +/−15% of the duration indicated.

An antimicrobial composition may be applied to a surface, solution, or substance, together with application of NSEPs as disclosed, in order to reduce a number of viable microbes on said surface or in such solution or substance, in accordance with the present disclosure. In an example, an antimicrobial may be applied or administered to a living subject such as a human and NSEPs applied in accordance with the present disclosure. For example, an acute, chronic, sub-acute, sub-chronic, treatment-refractory, or other microbial infection, such as a bacterial or fungal infection, may be present in a subject such as a human subject. An antimicrobial composition may be applied or administered to such subject and NSEPs applied to reduce a number of viable microbes, such as to eliminate, remove, reduce, ameliorate, or otherwise treat such infection. In another example, such infection may be anticipated or a risk of such infection may be present, such as in an immunocompromised subject, or in conjunction with surgery or wound or trauma, or known or expected exposure to an infectious microbe, whereupon an antimicrobial composition may be administered with application of NSEPs prophylactically, to prevent development of infection or proliferation of an infectious seed of microbe that may be present or suspected of being present. Such examples are included with reducing an amount of viable microbes as the term is used herein.

An antimicrobial composition may be administered by any of various medically known or accepted or approved means of applying or administering such antimicrobial composition. Examples include oral, parenteral (including subcutaneous, intradermal, intramuscular, intravenous and intraarticular), rectal and topical (including dermal, buccal, sublingual and intraocular) administration. An antimicrobial may be formulated as appropriate for such administration, which may be tailored to a given purpose, such as in a tablet, capsule, or other form for oral administration or injectable formulation for injection, or gel, cream, powder, ointment, or other composition for rectal or dermal application, etc. In some examples, one or more antimicrobial may be included in the surface of a material or an apparatus to be implanted on or within the body of a subject such as a human subject configured or otherwise formulated to have or promote an antimicrobial effect at the surface of such material or apparatus or to be released therefrom and have such an antimicrobial effect in tissue in the vicinity of such material or apparatus.

In accordance with an aspect of the present disclosure, NSEPs may be administered to such a subject so as to enhance an antimicrobial effect of such antimicrobial composition and reduce a number of viable microbes. For example, a subject may receive or may have received systemic treatment with an antimicrobial composition such that application of NSEPs to a part of the subject's body enhances an antimicrobial effect of said antimicrobial composition on microbes present where NSEPs are applied, reducing a number of viable microbes. In another example, an antimicrobial composition may be topically applied, such as in a cream or ointment or powder or other form, or locally injected, or present in a material or apparatus implanted or to be implanted, and NSEPs applied at a site of antimicrobial thereby applied, to enhance antimicrobial effectiveness or otherwise reduce a number of viable microbes there. Skilled persons would comprehend that various ways to apply antimicrobial compositions could be used in accordance with an aspect of the present disclosure.

In an example, an antimicrobial composition or substance may be applied or present at a concentration, or to achieve a concentration locally, that alone does not have an effect on a number of viable microbes at a given site. In another example, an antimicrobial composition or substance may be applied or present at a concentration, or to achieve a concentration locally, that alone has only low effect on a number of viable microbes at a given site. In either example, in accordance with an aspect of the present disclosure, applying NSEPs may increase a reduction in a number of viable microbes otherwise resulting from application of the antimicrobial composition in the absence of NSEPs. An antimicrobial composition may be administered at a concentration that is not effective at all or only minimally effective at reducing a number of viable microbes of a given species or strain when applied in the absence of NSEPs, whereas combining such administration with application of NSEPs cause an increase in reduction of viable microbes. In another example, NSEPs may be ineffective or only marginally effective or their own in reducing a number of viable microbes on their own but rendered effective in the presence of an antimicrobial composition. In both examples, neither an antimicrobial on its own or NSEP administration on its own may be effective in reducing a number of viable microbes whereas the combination of both is. In other examples, application of one or the other, or each, on its own may be somewhat effective but combined administration of both antimicrobial composition and NSEP may be more effective in reducing a number of viable microbes than either alone.

In another example, a time frame required for effectiveness of an antimicrobial composition in reducing a number of viable microbes may be reduced when administered in combination with application of NSEPs. Conventionally, an antimicrobial composition such as an antibiotic or antifungal may require hours, days, or even weeks to be effective in reducing a number of viable microbes, or to be fully effective in preventing or eliminating an infection. Surprisingly, as demonstrated herein, an antimicrobial composition may show substantial effectiveness in reducing a number of viable microbes in a short time frame, such as within an hour or less, following brief application or applications of NSEPs. Thus, whereas a given concentration of an antimicrobial composition may be effective in reducing a number of viable microbes on its own, combining its administration with application of NSEPs as disclosed herein may result in reduction of a number of viable microbes following a shorter time span of exposure to the antimicrobial composition at that concentration than would otherwise be required before such an effect of the antimicrobial composition results.

EXAMPLES

The following examples are intended to illustrate particular embodiments of the present disclosure but are by no means intended to limit the scope thereof.

Synergistic Effects of NSEPS and Antibiotics

Equipment. Used was a capacitor based Blumlein pulse generator with a spark gap switch to produce trapezoidal EPs of 300 ns duration at the peak with rise and fall times close to 50 ns. Multiple pulses were delivered at a frequency of 1 Hz.

The samples were treated in a standard electroporation cuvette (Dot Scientific) whose resistance must match the pulse generator's impedance to prevent pulse reflection. Utilizing Luria broth, containing 0.5% NaCl, in a cuvette with gap distances of 1 mm and 2 mm yielded the best electrical match (no reflections in the measured signal). Used were 2 mm cuvettes to ensure consistency between tests, and the applied voltage was measured across the cuvette using a LeCroy PPE 20 kV high voltage probe with a 1000:1 attenuation feeding into a TeleDyne LeCroy Waverunner 6 Zi Oscilloscope capable of measuring signals up to 4 GHz. Assuming a purely parallel plate geometry with minimal fringing gives an electric field E=V/d, where V is the peak voltage of the applied pulse and d is the gap distance.

Sample Preparation. These experiments assessed *Staphylococcus aureus* (gram positive bacterium number 25923) from ATCC and *Esherichia coli* (gram negative bacterium number 25922) inoculated in luria broth (LB Broth Lennox, powder microbial growth medium, SIGMA-ALDRICH) by taking 8 mL of broth in a 50 mL sterile conical tube and incubating in a shaker for 20 h at 37° C. The sample was then diluted with fresh Luria broth until attaining an optical density of 0.25 for 100 µL on a photospectrometer (Molecular Devices) for a wavelength of 562 nm as measured in a 96-well plate. The optical density, which varies with growth or tube volume, was determined experimentally and set between $1\times10^8$ and $1.5\times10^8$ colony forming units (CFUs)/mL for the samples to be pulsed. These samples were then plated at dilutions between $10^{-6}$ and 100 (no dilution) depending on the effectiveness of the pulse treatments.

Electric Pulse Treatment Protocol. Bacterial samples were then placed into the 2 mm cuvettes and treated with various EP parameters determined comparable to those in the literature (Perni et al. 2007) and selected such that that the highest electric fields induced clinically relevant inactivation (4 log-10) and lower electric fields induced insignificant inactivation (less than 0.3 log-10, or 30%). Although no consensus exists on a universal scaling law for applied EP "dose," we fixed the energy density $$U=NE^2\tau, \qquad (1)$$

where N is the number of pulses and $\tau$ is the pulse duration. Fixing U for E=40, 30, and 20 kV/cm gave N=250, 445, and 1000 pulses, respectively. Cultures were plated as described below.

Cuvettes were filled with 365 µL of sample (sufficient to just cover the electrodes) and then 250 µL of molecular biology grade mineral oil was placed on top. Keeping the samples on ice upon achieving the required dilution further reduced experimental variability by slowing biological processes, such as fission. This facilitated the assessment of the inactivation efficiency of EPs, drugs, and combined treatments.

Tests used the clinically relevant, bactericidal drug tobramycin, which targets the 30S and 50S ribosome complex and has a clinical dose from 4 to 5 µg/mL and rifampicin, which inhibits bacterial dependent RNA polymerase. Added were 0.2, 2, and 20 µg/mL of each drug to the initial bacterial dilutions prior to pulsing. Samples were immediately placed on ice to minimize cell division and reduce variability. These aliquots were also used to plate individual unpulsed controls for each drug concentration.

Plating. Plating was done on standard disposable tissue culture Petri dishes from VWR (15 cm diameter, 10 mm height) and covered with 10 mL of agar in luria broth (Agar, microbiology tested powder, SIGMA-ALDRICH), which was prepared by adding 20 g of LB lennox (SIGMA-ALDRICH) and 15 g/L of agar to water and then autoclaved.

Plated were samples at dilutions of $10^{-6}$ and $10^{-3}$ for low and high electric field treatments, respectively, and at $10^{-6}$ and $10^{-5}$ for controls. All samples containing 100 µL of pulsed or diluted cultures were plated on LB agar plates and counted after overnight incubation at 37° C.

Pulsing without drugs: Assessed was the impact of EPs on colony forming units (CFUs) to serve as a baseline for comparing experiments combining EPs and drugs. Table 1 summarizes the resulting population reduction for both *S. aureus* and *E. coli* for six replicates for the control and 20 kV/cm conditions and four replicates for the 30 kV/cm and 40 kV/cm experiments.

TABLE 1

Electric pulse parameters and the subsequent reduction in *S. aureus* and *E. coli* populations.

| Electric Field (kV/cm) | # Pulses | Log reduction of S. aureus | Log reduction of E. coli |
|---|---|---|---|
| 0 | 0 | 0.0 ± 0.0 | 0.0 ± 0.0 |
| 20 | 1000 | 0.2 ± 0.1 | 1.42 ± 0.39 |
| 30 | 445 | 2.9 ± 0.7 | 3.26 ± 0.30 |
| 40 | 250 | 3.7 ± 0.7 | 3.81 ± 0.0 |

EPs induced greater cell death for *E. coli* than for *S. aureus* until the 40 kV/cm. Despite each treatment delivering the same energy density (c.f. Eq. (1)), the applied electric field clearly drove the resulting cell death, as observed previously when assessing the impact of bipolar EP induced ion transport, for each microorganisms with the effect starting to plateau at 40 kV/cm for *E. coli*. The rapid increase in CFU reduction observed from 20 kV/cm to 30 kV/cm for each microorganism suggests a threshold for membrane effects. Electroporation threshold occurs for membrane voltages on the order of a few hundred millivolts with longer durations and higher voltages responsible for making this permeabilization irreversible.

Thus, simply applying additional lower intensity EPs, even when these pulse train deposits the same total energy as the higher intensity EP train, may be inadequate to inactivate microorganisms. This suggests that the time between the pulses (~1 s) may be sufficiently long compared to the membrane pore sizes and lifetimes (particularly for nanosecond duration EPs, which typically create smaller pores than conventional electroporation) for additional EPs to further permeabilize the membrane. Thus, the pores formed by lower intensity EPs may be too small for irreversible pore formation and the time between pulses may be sufficiently long so that subsequent pulses do not induce irreversible pore formation. Thus, subsequent low intensity EPs may be primarily creating new pores and cells can counter this effect by reestablishing homeostasis of ions and H+ ions between pulses after the nanopores collapse.

Pulsing with drugs: bacterial samples of both gram-positive *S. aureus* and gram-negative *E. coli* strains were pulsed in a solution with 0.2, 2, and 20 µg/mL of tobramycin and compared to an un-pulsed drug-exposed control. Pulsing and plating were performed to ensure that the drug exposure time of the bacteria was approximately fifteen minutes.

FIG. 1 shows that combining trains of 300 ns EPs with tobramycin induces significantly greater inactivation of *S. aureus* than the antibiotic alone. As noted above, even though each train of pulses delivered the same total energy to the sample, the greatest microorganism inactivation arose for the higher electric fields strengths. Combining the 20 kV/cm EPs with no drug or 0.2 µg/mL induced a 10-20% reduction in *S. aureus* population. Combining these EP with higher, clinically relevant concentrations of 2 µg/mL and 20 µg/mL resulted in 1.5 and 2.6 log-reduction, respectively, which were statistically significant compared to treatments of just tobramycin. Although the 30 kV/cm and 40 kV/cm conditions resulted in statistically significant inactivation compared to the untreated control, microorganism inactivation still increased with increasing concentration of tobramycin.

Figure 2:
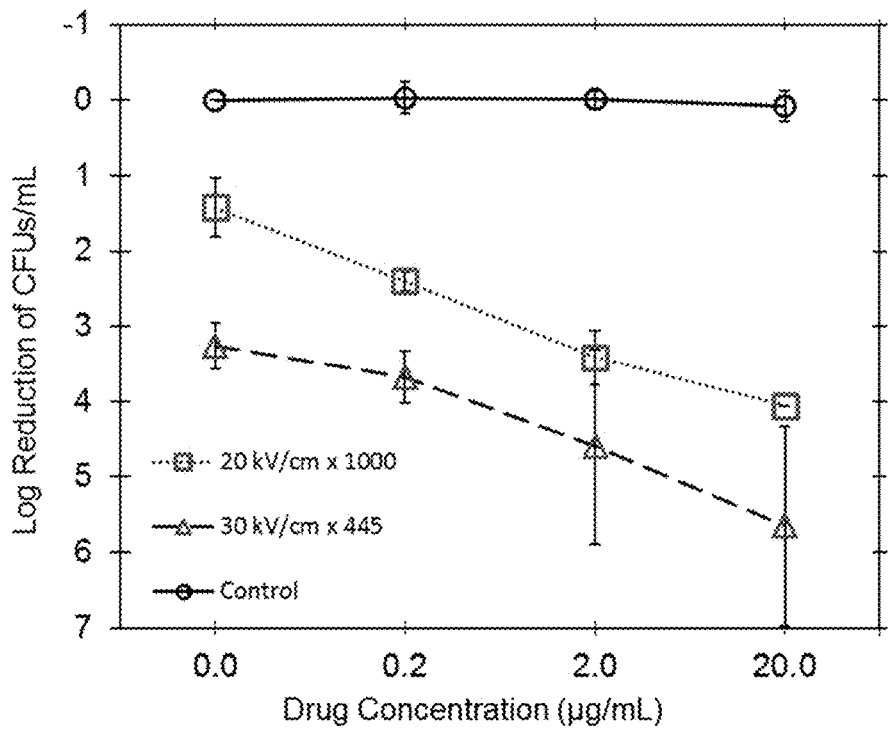
FIG. 2 shows effects of combining trains of 300 ns electric pulses with the same energy, but different electric fields and number of pulses, with different concentration of the antibiotic tobramycin synergistically reduced an amount of viable E. coli with the effect stronger for higher electric fields.

FIG. 2 shows that combining trains of 300 ns EPs with 2 and 20 µg/mL of the bactericidal tobramycin induces significantly greater inactivation of *E. coli* than the antibiotic alone. For 0.2 µg/mL tobramycin, the 30 and 40 kV/cm treatments exhibited synergy while the 20 kV/cm treatment did not. The EPs induce a noticeably greater inactivation of *E. coli* than *S. aureus*. The 20 kV/cm condition induced a statistically significant reduction of 1.4 log-10 for the *E. coli* samples with no drug compared to sub-log reduction observed for *S. aureus*. Likewise, the 30 kV/cm treatment with no drug induced a 3.5 log-reduction of CFUs, which is a full log-reduction more compared to the *S. aureus*. Combining 40 kV/cm EPs with antibiotics resulted in reductions of over 9 log-10 and was considered a complete sterilization of the *E. coli*. As for *S. aureus*, increasing the drug concentration enhanced microorganism inactivation.

Figure 3:
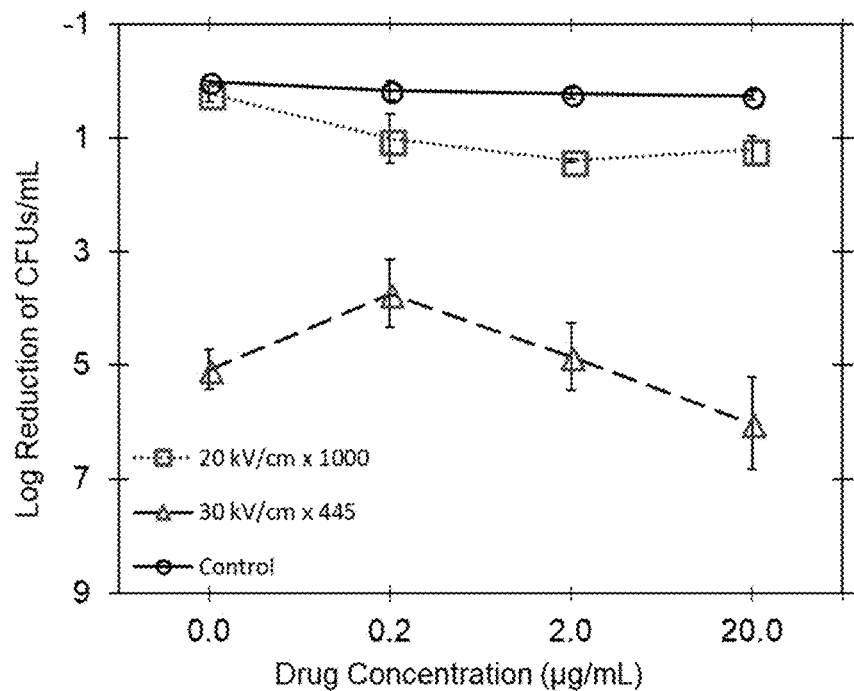
FIG. 3 shows effects of combining trains of 300 ns electric pulses with the same energy, but different electric fields and number of pulses, with different concentration of the antibiotic rifampicin synergistically reduced an amount of viable S. aureus.

FIG. 3 shows the impact of rifampicin on *S. aureus* inactivation. Combining the 20 kV/cm EPs with no drug induced a minimal reduction in *S. aureus* population. Applying ¹/₅₀th of the clinical dose of 10 or 0.2 µg/mL, and more clinically relevant concentrations of 2 and 20 µg/mL induced 1-log reduction. The 30 kV/cm treatment exhibited a greater clinical significance with the 20 µg/mL dose, causing an additional 1.5 log-reduction in 10 min.

Figure 4:
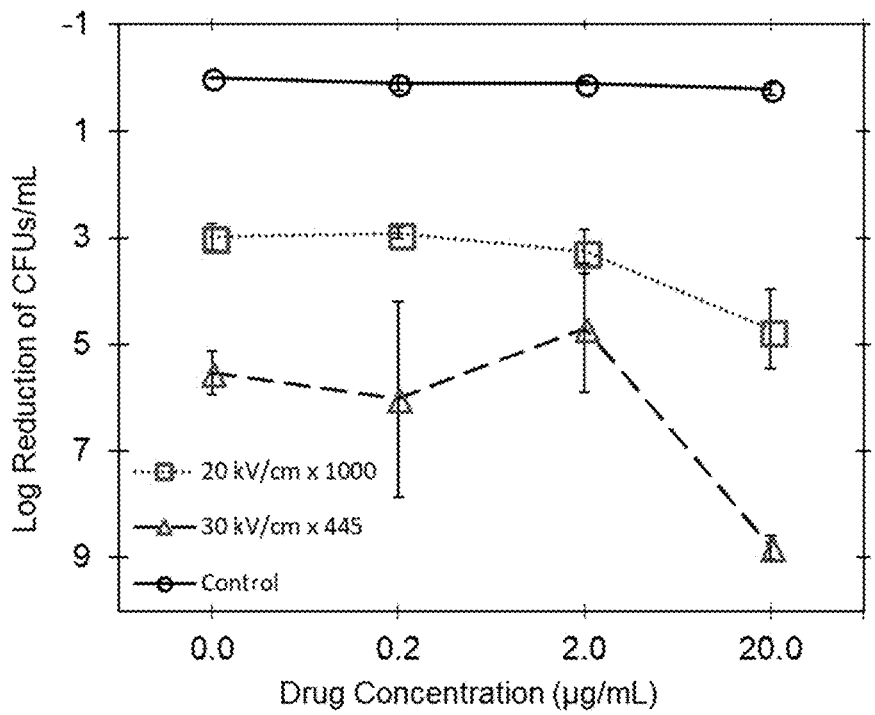
FIG. 4 shows effects of combining trains of 300 ns electric pulses with the same energy, but different electric fields and number of pulses, with different concentration of the antibiotic rifampicin synergistically reduced an amount of viable E. coli.

FIG. 4 shows the impact of rifampicin on *E. coli* inactivation. Applying 300 ns EPs enhanced the effectiveness of rifampicin in inhibiting *E. coli* growth. Combining EPs with concentrations of 2 and 20 µg/mL induced an additional 1.5 log-reduction compared to pulsing alone. Over a 9-log reduction, consistent with complete sterilization, occurred when combining 20 µg/mL rifampicin with 445 pulses of 30 kV/cm field. Compared to the inactivation due strictly to 20 µg/mL rifampicin with no EPs, the EPs induced a 4-log synergy (additional kill off) compared to just the rifampicin.

Figure 5A:
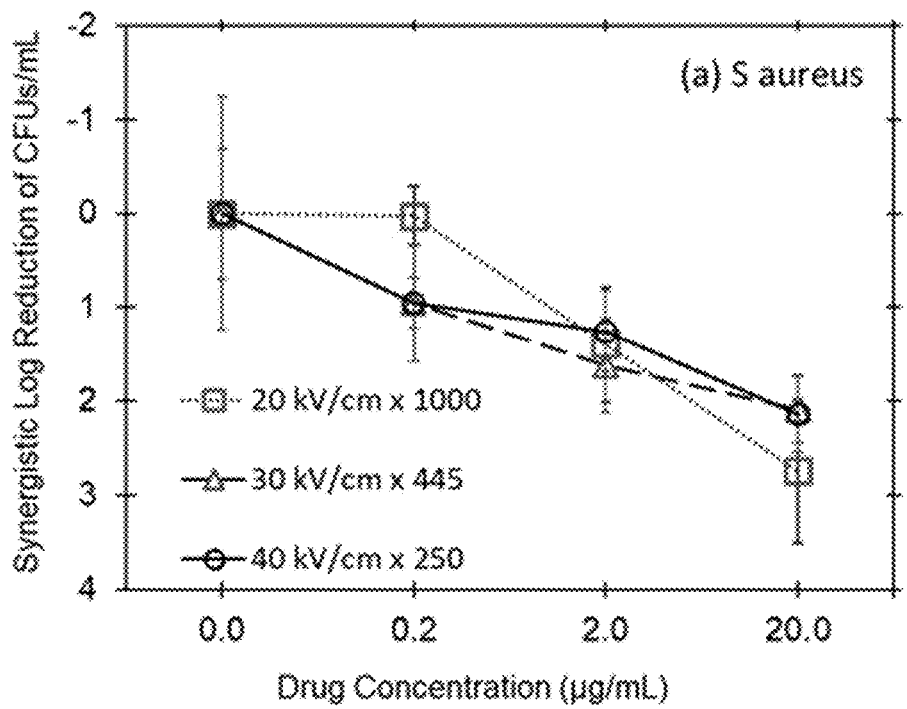
FIG. 5A shows effects of combining trains of 300 ns electric pulses with the same energy, but different electric fields and number of pulses, with different concentration of the antibiotic tobramycin synergistically reduced an amount of viable S. aureus.
Figure 5B:
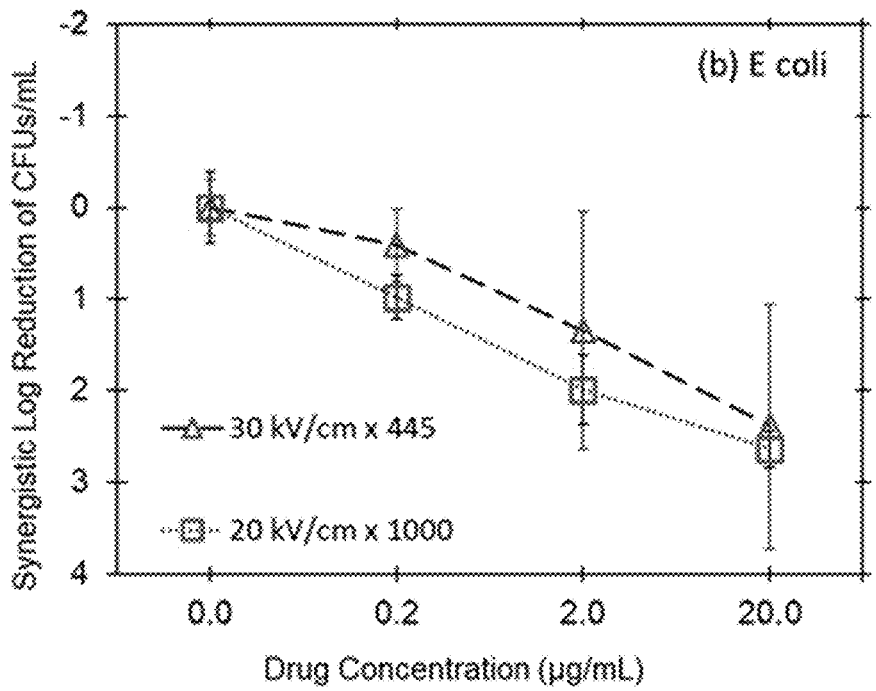
FIG. 5B shows effects of combining trains of 300 ns electric pulses with the same energy, but different electric fields and number of pulses, with different concentration of the antibiotic tobramycin synergistically reduced an amount of viable E. coli.

Synergy between antimicrobial composition application and NSEP application may be quantified as the additional inactivation induced by the antimicrobial for a given pulse condition. In addition to the synergy in the quantity of cell death, the time for inactivation to occur is also dramatically reduced. While the standard clinical dose of 4-5 µg/mL of tobramycin induces a noticeable kill-off of bacteria, this effect takes many hours. Combining even ¹/₂₀th (0.2 µg/mL) of this dose with a train of NSEPs causes a 1.5 to 2.5 log-reduction after only 15 min of exposure to the antibiotic. FIGS. 5A-5B shows the resulting synergy for tobramycin for the EP parameters described above. For *S. aureus* (FIG. 5A), no synergy occurred for the 20 kV/cm pulse trains for tobramycin concentrations at 0.2 µg/mL, while 2.0 µg/mL resulted in 1.5 log synergy. For the 30 and 40 kV/cm pulse trains, synergies occurred for all 2 and 20 µg/mL doses of tobramycin and increased with increasing concentration. Interestingly, the synergy for tobramycin concentrations at or above 2 µg/mL was essentially independent of the applied field, although the net inactivation depended strongly on the applied electric field [c.f. FIG. 1]. For *E. coli*, FIG. 5B shows that pulse trains using any of the applied electric fields experienced synergy for any tobramycin concentration with the synergy increasing for increasing drug concentration and relatively insensitive of applied field for both the 20 and 30 kV/cm cases. In this case, the synergy appears to decrease for the 40 kV/cm train when tobramycin concentration is increased from 0.2 to 2.0 µg/mL since the total number of viable cells after 40 kV/cm treatments is less than 2-log from the original 9-log of cells at the beginning of the experiment.

While one may consider synergy as increasing inactivation by incorporating NSEPs to antibiotic treatment, viewing synergy as a method of boosting antibiotic effectiveness by reducing time to action has serious implications in infection treatment. Inducing the effect that an antibiotic would have over a 12 or 24-h period in a matter of seconds to minutes dramatically reduces treatment time, which can be critical for fast-acting infections or infections that are difficult to treat with such slow treatment modalities, such as those causing rapid cellulitis. Boosted synergy also implies that lower doses of last-line of defense drugs, which can have serious side effects, can be used to induce the same effects as current clinical doses or prophylactic dose levels. The ability of EPs to permeabilize bacterial membranes to improve the effectiveness of antimicrobials may reduce the number of cells available to develop resistance.

In these examples, the entire process, including pulsing the sample and diluting and plating the colonies, took approximately 15 min. Synergy occurred for ¹/₂₀th, 0.2 µg/mL, of the recommended clinical dose of tobramycin, 4 µg/mL, with dramatic synergy arising for higher doses. The significance of this EP-induced synergy is twofold. First, this process will reduce the antibiotic dose and electrical energy input needed to treat infections and preserve host tissue. Second, the EP may weaken the microorganisms or sufficiently facilitate passive drug transport into the cell to allow the application of antibiotics usually ineffective against certain types or strains of bacteria due to the drug's size or resistance mechanisms present in the bacteria.

Electrochemotherapy, where EPs permeabilize tumors to chemotherapeutics to enhance treatment efficacy, often use needle electrodes, interlocking grid patterns of electrodes printed on surfaces, or circular electrode designs with a needle electrode surrounded by a cylindrical opposite polarity electrode. Comparable configurations may be applicable in accordance with aspects of the present disclosure. Miniaturized electrode designs or flexible electronic surfaces (e.g., in the form of a wand for application at wound sites) may be used as well. Integrating these electrode designs with drip systems that can deliver drugs or combination of drugs from vials based on the infection under treatment is also included.

Figure 6:
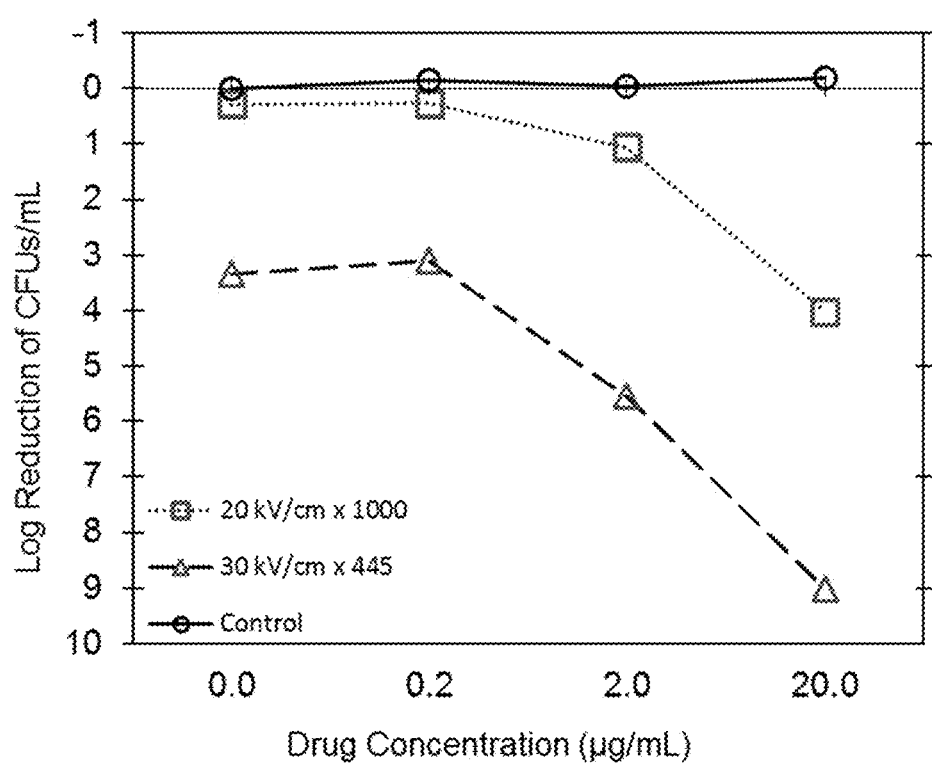
FIG. 6 shows effects of combining trains of 300 ns electric pulses with the same energy, but different electric fields and number of pulses, with different concentration of the antibiotics tobramycin and rifampicin (same concentration of each drug) synergistically reduced an amount of viable methicillin-resistant S. aureus.
Figure 7:
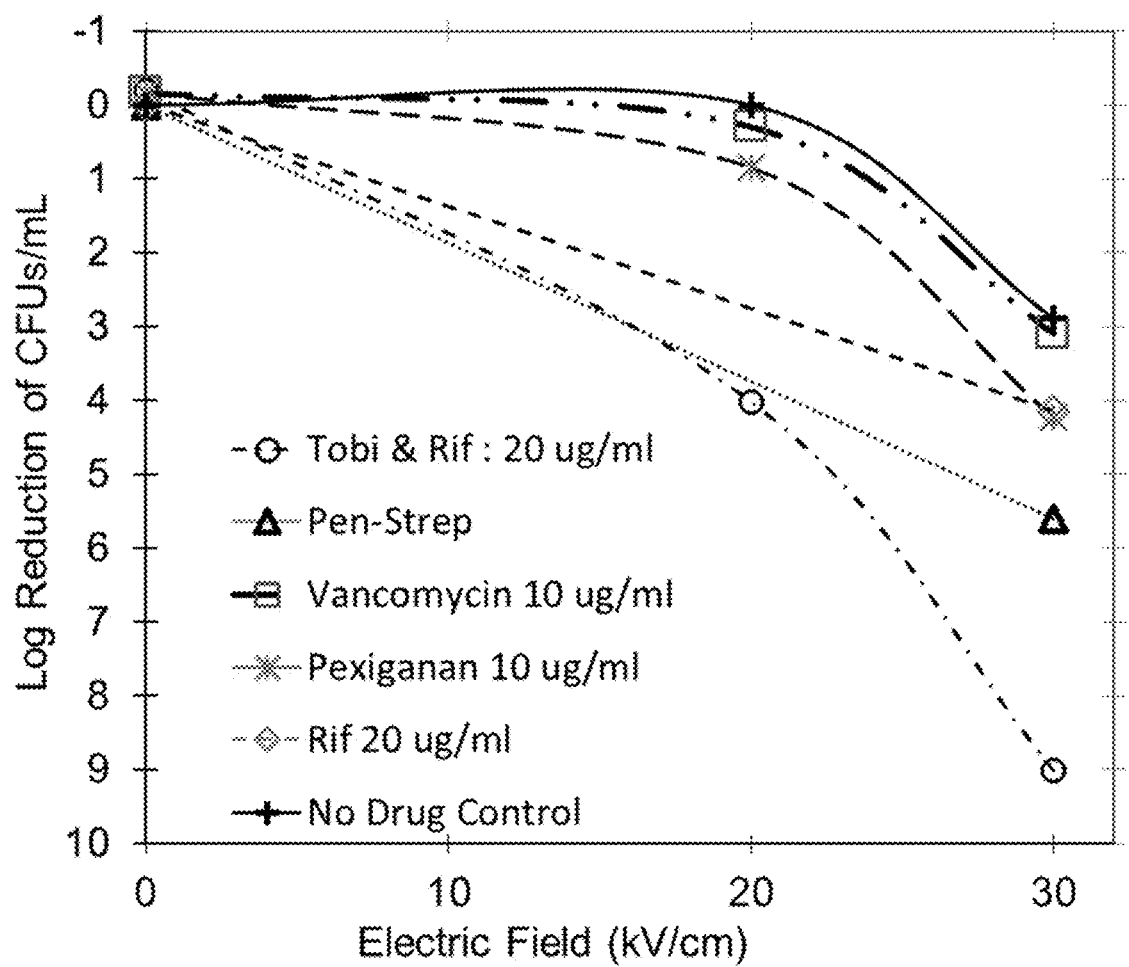
FIG. 7 shows synergistically reduced amount of viable methicillin-resistant S. aureus under 300 ns electric pulses combined with administration of different antibiotics.

FIG. 6 shows the synergistic inactivation of Methicillin Resistant *Staphylococcus Aureus* (MRSA) under 300 ns EPs with combined application of tobramycin and rifampicin (same concentration of each drug). FIG. 7 shows the effect of 300 ns EPs on MRSA in synergy with different drugs. As shown by conditions without NSEP administration, or with antibacterial dosing that did not show antibacterial effectiveness within this time frame, as compared to reductions in CFU when NSEP and antibacterial compositions were applied in combination, the two types of treatment worked synergistically to produce an antimicrobial effect measurably obtained and demonstrated over a short time frame.

Effects on Gram-Negative Bacteria of Gram-Positive Antibacterials in Combination with NSEPS Methodology was comparable to the foregoing examples. Except for rifampicin, the five other antibiotics in these examples primarily target gram-positive bacteria and are largely ineffective or not used against gram-negative bacteria in a clinical setting.

A Blumlein pulsed generator consisting of two lines comprised of twelve 2000 pF capacitors connected by inductors produced 300 ns EPs with rise-times of 30 ns and fall-times of 35 ns at a repetition frequency of 1 Hz (12). The EPs were applied to a standard 2 mm gap electroporation cuvette (Dot Scientific®) filled with a solution containing the microorganisms. Used was a Luria broth of 0.5% salinity (5 grams of NaCl/Liter) for the solution to electrically match the resistance of the sample with the impedance of the pulse generator (11Ω) to prevent signal reflection. The voltage measurements were taken using a LeCroy PPE 20 kV high voltage probe with a 1000:1 attenuation recorded by a TeleDyne LeCroy® Waverunner 6 Zi Oscilloscope with a bandwidth of 4 GHz.

Sample Preparation:

NSEPs were combined with gram positive antibiotics to enhance the inactivation of three clinically relevant antibiotic resistant gram-negative strains of bacteria and one gram-positive strain. The gram-negative strains included a carbapenem-resistant *Escherichia coli* (ATCC® BA-2452™, New Delhi metallo-beta-lactamase NDM-1 positive), *Klebsiella pneumoniae* (ATCC® BAA-2146™ NDM-1 positive), and a gentamicin, streptomycin and sulfonamide resistant *Pseudomonas aeruginosa* (BEI Resources NR-31040). Assessed was the gram-positive strain of methicillin resistant *Staphylococcus aureus* (USA300-0114 strain), which is also resistant to erythromycin and tetracycline. Samples were cultured in Luria broth (LB Broth Lennox, powder microbial growth medium, SIGMA-ALDRICH®) by taking 25 mL of broth in a 50 mL sterile conical tube and incubating in a shaker for 16 h at 37° C. Samples were diluted 50% by adding 25 mL media to the incubated sample as we plated controls for each experiment and condition.

The examples assessed the following antibiotics: vancomycin, linezolid, rifampicin, mupirocin, erythromycin, and fusidic acid. These antibiotics are primarily used against gram-positive bacteria because they cannot effectively traverse the membranes of gram-negative bacteria. Vancomycin is used primarily to treat gram positive bacteria like MRSA, MRSE, and other resistant strains of enterococci. Linezolid is used primarily against gram-positive bacteria like MRSA, vancomycin resistant enterococci and streptococci. Mupirocin is used primarily to treat MRSA and other *S. aureus* strains, with mupirocin resistant *S. aureus* arising almost immediately after clinical trials. Erthromycin is bacteriostatic in nature, and while its mechanism is incompletely understood, it acts internally by binding to the 50S subunit of the rRNA complex and is also used primarily against gram-positive bacteria. Fusidic acid is another bacteriostatic compound used primarily to treat gram-positive bacteria with MRSA and SA strains exhibiting resistance. Of the antibiotics studied here, the WHO Model list of essential medicines includes rifampicin and vancomycin and classifies linezolid as a drug of last resort.

Electric Pulse Treatment Protocol:

Samples were treated in 2 mm gap cuvettes containing 365 μL of sample between the electrodes, with bio-grade mineral oil added on top of the electrode plates to prevent arcing. This examples includes starting with a low electric field that induced minimal inactivation alone, but did when combined with antibiotics at dosages that were also insufficient to induce inactivation alone. These results were compared to a higher electric field capable of inactivating bacteria independently with varying effectiveness across strains.

To establish a common baseline for comparing different NSEP parameters, we fixed the energy density U delivered to the cuvettes according to Formula (1) (above). For 300 ns EPs, 500 EPs at 20 kV/cm and 222 EPs at 30 kV/cm delivered the same energy to the sample.

Plating:

Tissue culture Petri dishes from VWR® (15 cm diameter, 10 mm height) were utilized for plating. Each plate was covered with 15 mL of Luria broth (Agar, microbiology tested powder, SIGMA-ALDRICH®), which was prepared by adding 20 g of LB Lennox (SIGMA-ALDRICH) and 15 g/L of agar to water prior to being autoclaved. The salinity of the agar was the same as the LB (0.5% NaCl) to minimize additional environmental stressors on the bacteria.

Removed was 20 μL from each cuvette and added to 180 μL of PBS in a 96-well dish in triplicate. Each well was then diluted by a ratio of 10:1 five additional times by taking 20 μL of the diluted sample into subsequent wells using multichannel pipettes (using fresh tips for each dilution). Plated were the six dilutions of each sample two times each by adding 4 μL from each well onto the Petri dish using a multi-channel pipette, which allowed the plating of all three replicates on the same plate to achieve n=6. These plates were then cultured overnight in an incubator at 37° C. and counted the next day.

Counts were taken for relevant dilutions (colony counts ranged from 15 to 25 colonies) and multiplied by $25 \times 10^{dilution}$, to account for the 4 μL plated for each condition. Examples were repeated three times each over different days with different incubated samples. Except for rifampicin, the five other antibiotics in these examples primarily target gram-positive bacteria and are largely ineffective or not used against gram-negative bacteria in a clinical setting.

Bacterial Inactivation Combining Electric Pulses (EPs) with Antibiotics

Figure 8A:
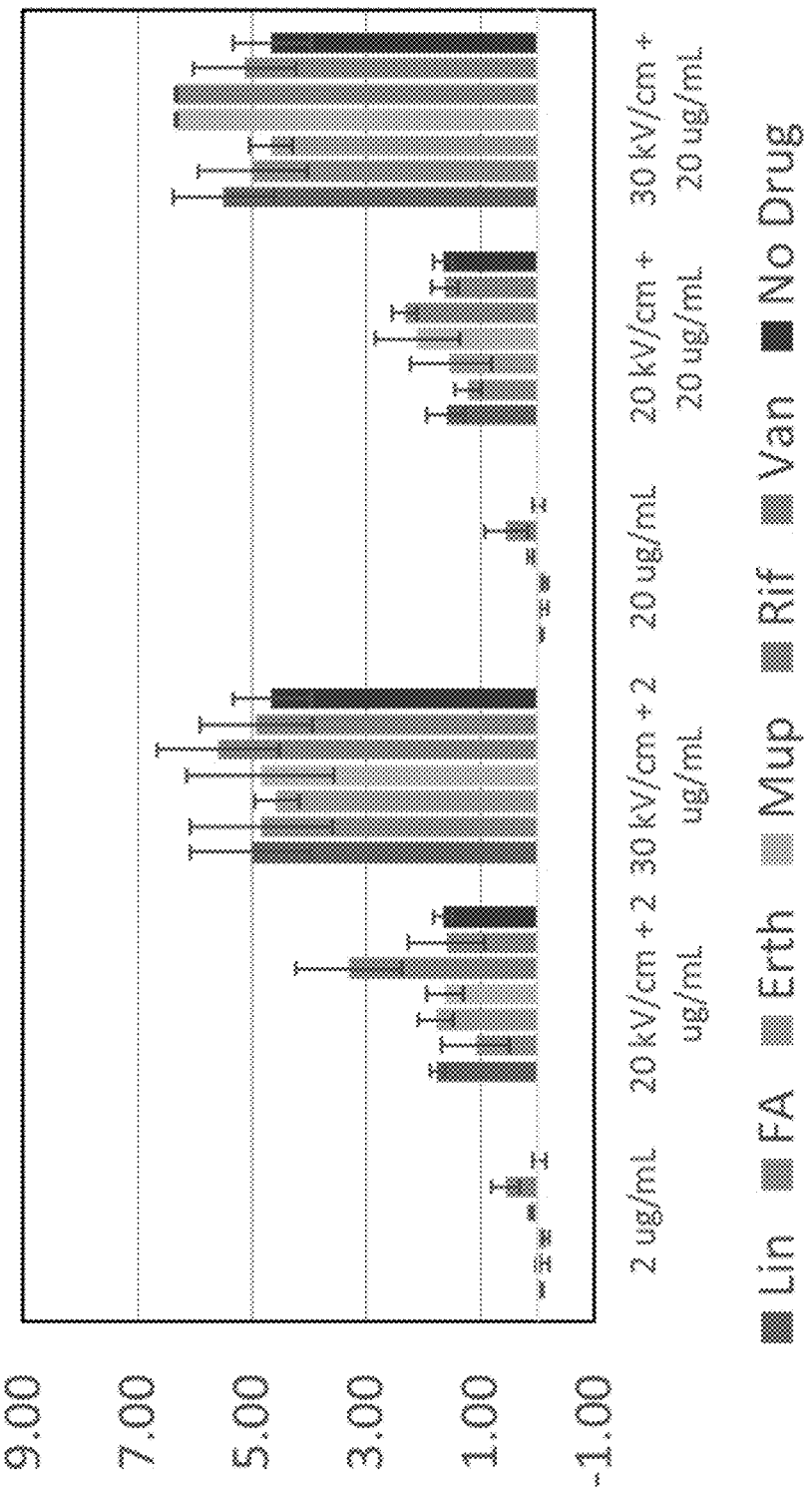
FIG. 8A and FIG. 8B show reduced amount of viable methicillin-resistant S. aureus following 300 ns electric pulses (EPs) (445 at 20 kV/cm or 222 at 30 kV/cm) and/or various concentrations of antibiotics (from left to right, Lin=linezolid, FA=fusidic acid, Erth=erythromycin, Mup=mupirocin, Rif=rifampicin, and Van=vancomycin).
Figure 8B:
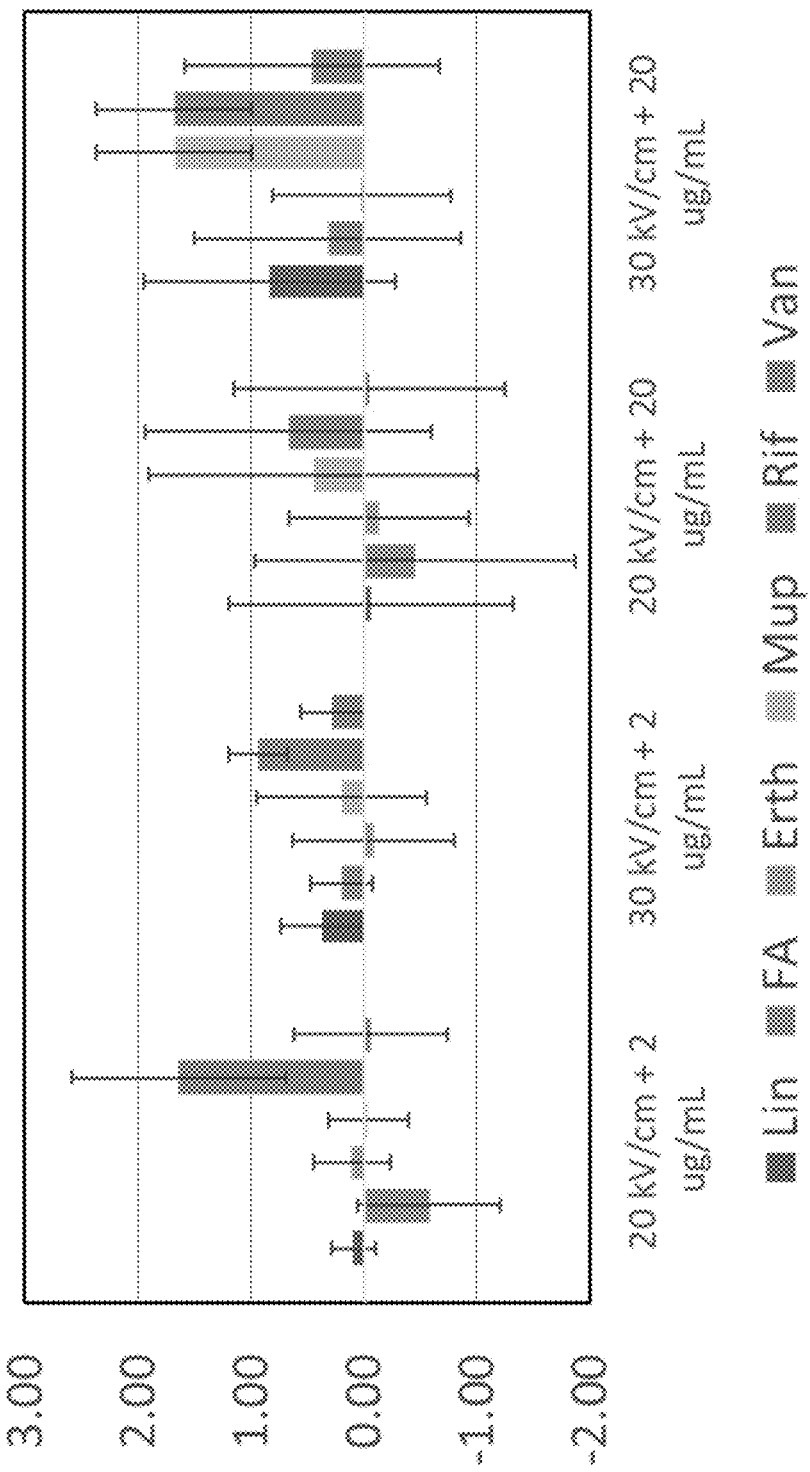

Assessed were various combinations of the antibiotics above with NSEPs for inactivating one gram-positive and three-gram negative bacteria. FIGS. 8A-8B highlight the inactivation of MRSA 300 under these conditions and the resulting synergy that arises from adding a single antibiotic to the NSEPs. Treating MRSA 300 with either 2 µg/mL or 20 µg/mL induced less than 1-log reduction in cell count. Applying either 445 20 kV/cm or 222 30 kV/cm 300 ns EPs induced over 1-log or 4-log reduction, respectively. Since these NSEPS had the same pulse duration and delivered the same overall energy density to the microbes, and the time between EPs of 1 s may be of sufficient for many pores to reseal, this suggests that higher electric field may have a dramatic effect on MRSA 300 inactivation. With all else equal, raising the electric field may increase membrane potential, making both reversible and irreversible electroporation more likely. Because only very long-lived pores will remain for either NSEP condition, the driving factor for membrane level effects will likely be the membrane potential from a single NSEP, suggesting that the 30 kV/cm should have the larger impact. FIG. 8A further shows that, for example, combinations of 2 µg/mL of rifampicin with the 20 kV/cm NSEPs and 20 µg/mL of mupirocin or rifampicin with the 30 kV/cm NSEPs yielded improvement on MRSA 300 inactivation compared to using only the NSEPs.

FIG. 8B shows the synergistic inactivation caused by adding antibiotics to the NSEPs. As anticipated from FIG. 8A, the largest synergy of approximately 1.5-log occurred when combining 2 µg/mL of rifampicin with the 20 kV/cm NSEPs and 20 µg/mL rifampicin and mupirocin with the 30 kV/cm EPs. The increased synergy of mupirocin with increasing electric field suggests that permeabilizing the membrane to facilitate its concentration in the MRSA may be particularly important for improved treatment outcomes since it is specifically designed to target MRSA.

Inactivating Gram-Negative Bacteria with Gram Positive Antibiotics

Figure 9A:
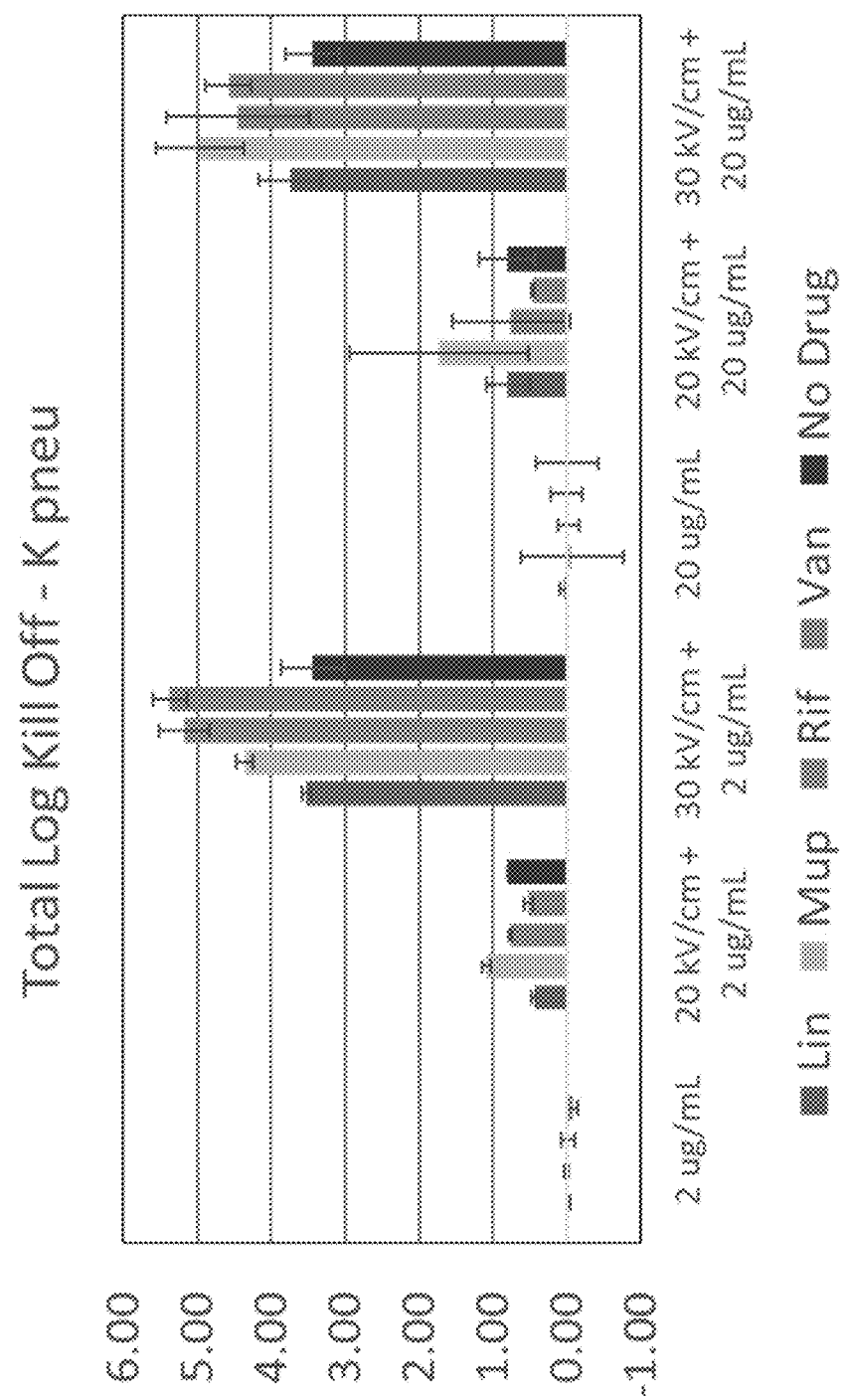
FIG. 9A and FIG. 9B show reduced amount of viable K. pneumoniae following treatment with 300 ns electric pulses (EPs) (445 at 20 kV/cm and 222 at 30 kV/cm) and/or various concentrations of antibiotics (from left to right, Lin=linezolid, Mup=mupirocin, Rif=rifampicin, and Van=vancomycin).
Figure 9B:
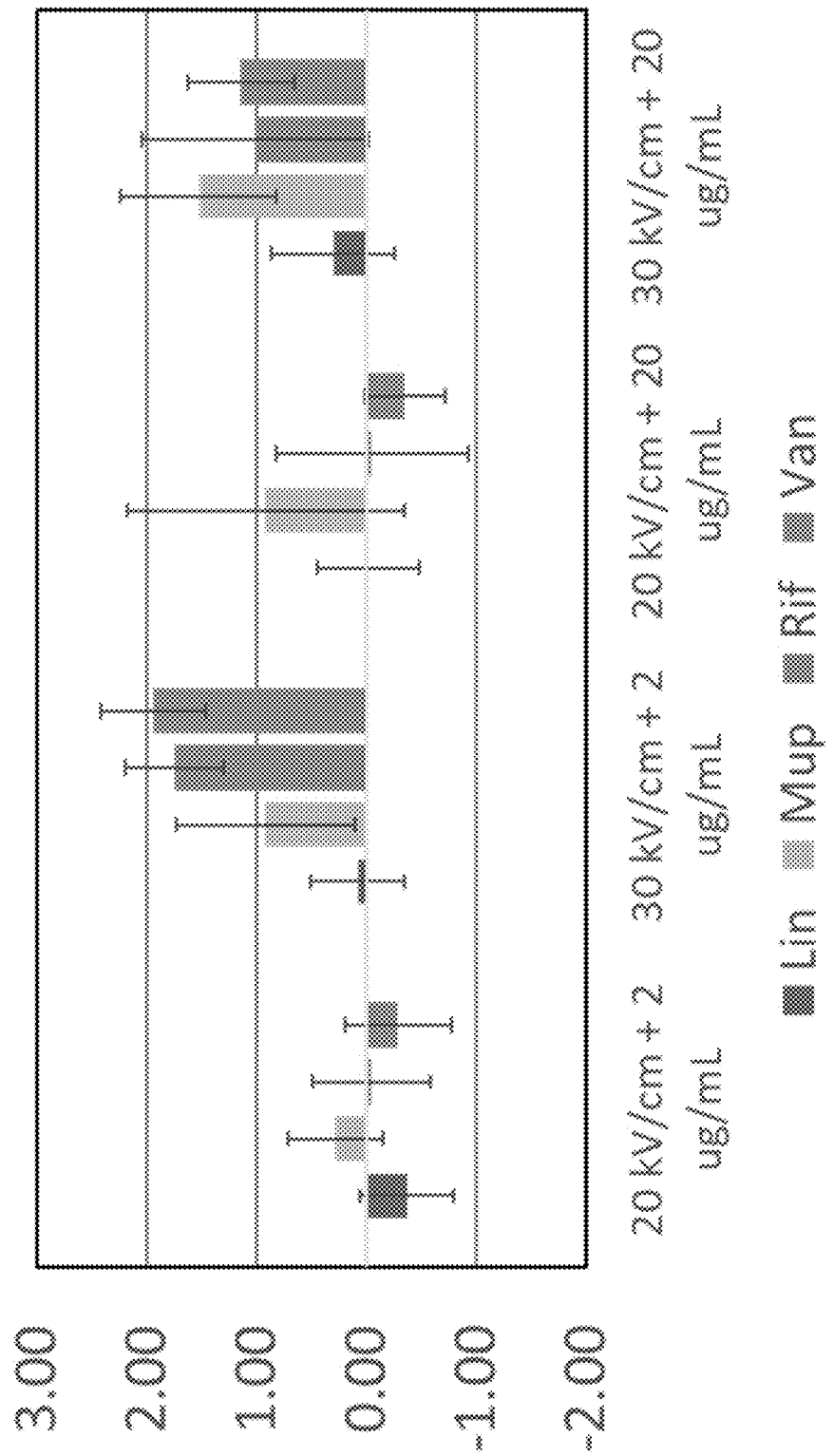

FIGS. 9A-9B show inactivation for the NSEPs and/or either 2 µg/mL or 20 µg/mL of linezolid, mupirocin, rifampicin, or vancomycin. 20 kV/cm NSEPs induce less than 1-log reduction in the gram-negative K. pneumoniae, while the 30 kV/cm NSEPs induce a statistically significant 3.5-log reduction. Applying 2 µg/mL or 20 µg/mL of the four drugs induced no statistically significant reduction in K. pneumoniae. Combining any of the drugs with the 20 kV/cm NSEPs induced a slight increase 2 µg/mL mupirocin and an increase for the 20 µg/mL mupirocin. For the 30 kV/cm NSEPs, adding 2 µg/mL of rifampicin or vancomycin induced 5-log reduction and 2 µg/mL induced a 4-log inactivation. Adding 20 µg/mL of mupirocin or vancomycin to the 30 kV/cm NSEPs induced over 4-log reduction that was an improvement over the NSEPs. Adding 20 µg/mL of either linezolid or rifampicin did not induce a statistically significant improvement over the NSEPs themselves.

FIG. 9B quantifies improvement by looking at the synergistic (additional) inactivation induced by the drugs compared to just the NSEPs alone. Combining the drugs with the 20 kV/cm EPs induced no additional inactivation. Combining 2 µg/mL of mupirocin, rifampicin, or vancomycin to the 30 kV/cm NSEPs induced 1-log additional inactivation that was a statistical significant improvement. Adding 20 µg/mL of mupirocin and vancomycin to the 30 kV/cm NSEPs induced over 1-log additional inactivation; adding 20 µg/mL of rifampicin induced 1-log additional inactivation. Thus, these results indicate that NSEPs can effectively make antibiotics that normally target gram-negative bacterial (mupirocin and vancomycin) more effective against a gram-negative bacterium than either the NSEPs or the drug alone.

Figure 10A:
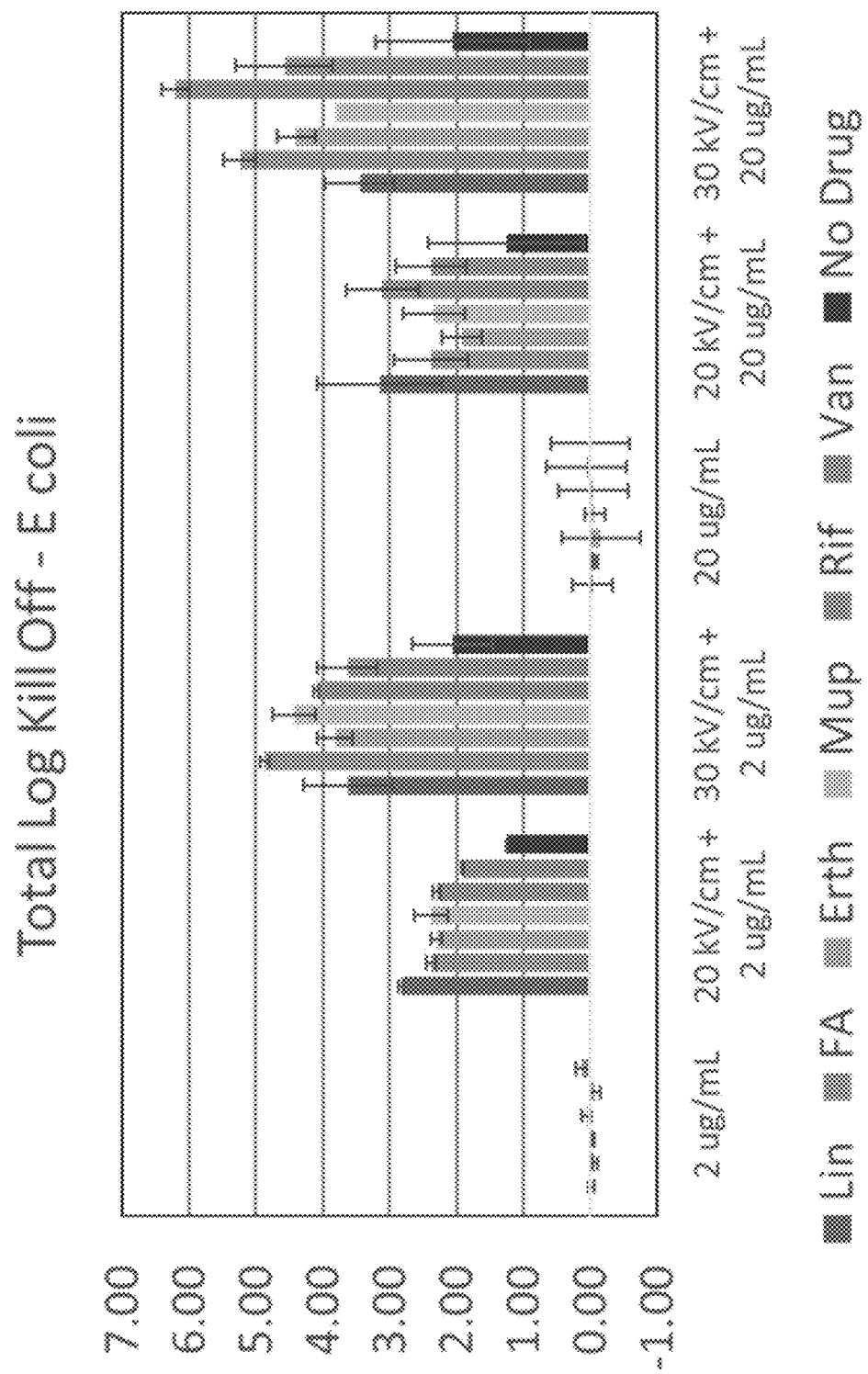
FIG. 10A and FIG. 10B show reduced amount of viable E. coli following treatment with 300 ns electric pulses (EPs) (445 at 20 kV/cm and 222 at 30 kV/cm) and/or various concentrations of antibiotics (from left to right, Lin=linezolid, FA=fusidic acid, Erth=erythromycin, Mup=mupirocin, Rif=rifampicin, and Van=vancomycin).
Figure 10B:
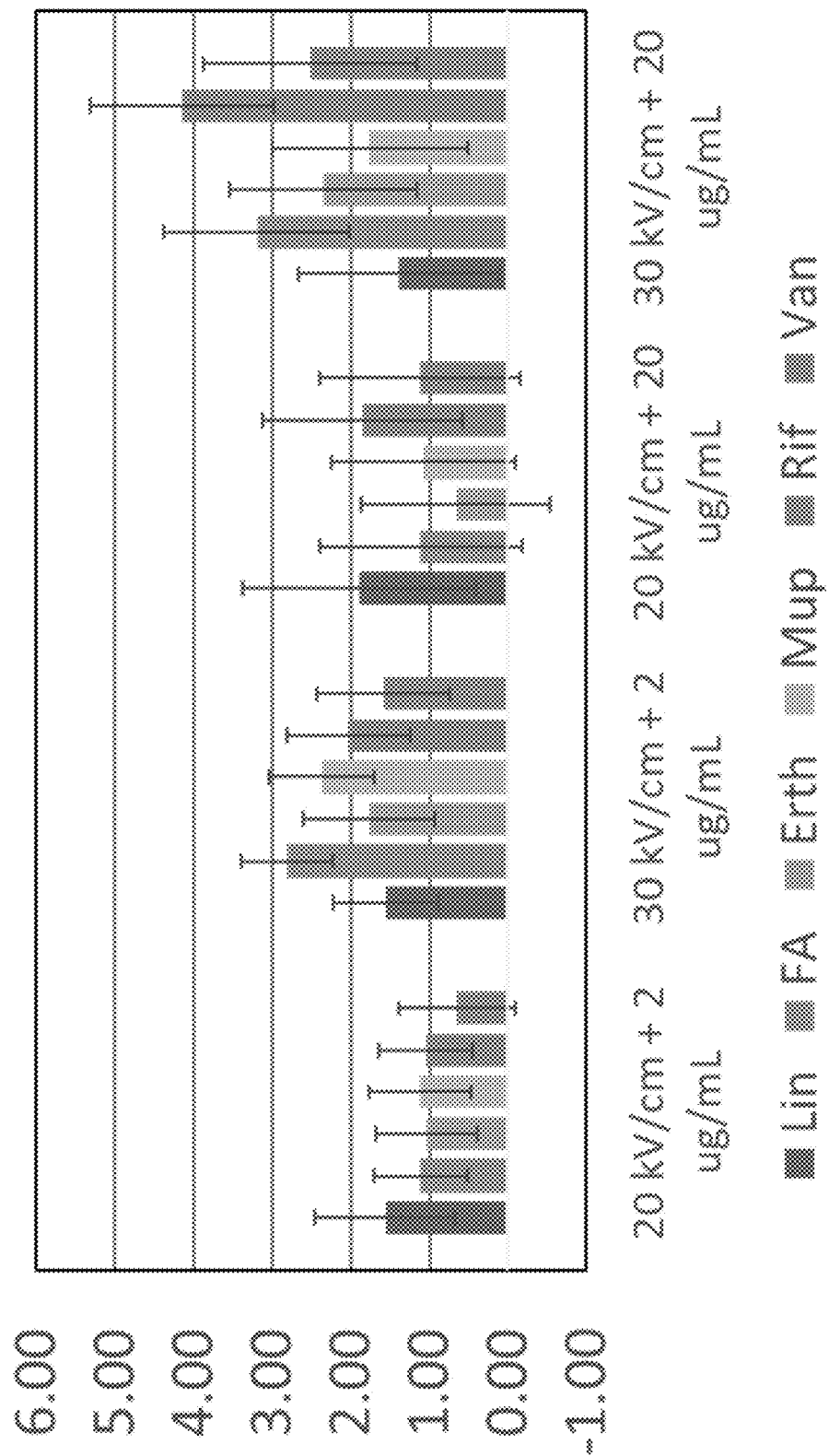

FIGS. 10A-10B show similar inactivation of gram-negative E. coli by gram positive antibiotics. Applying 2 µg/mL or 20 µg/mL of linezolid, fusidic acid, erythromycin, mupirocin, firampicin, or vancomycin induced changes in E. coli population. Applying the 20 kV/cm NSEPs induced a 1-log inactivation. Combining the 20 kV/cm NSEPs with these 2 µg/mL antibiotics inactivated between 2-log and 3-log E. coli compared to the NSEPs alone. Adding 20 µg/mL of these antibiotics induced similar levels of inactivation. The consistent inactivation levels when combining the 20 kV/cm NSEPs with the either 2 µg/mL and 20 µ/mL suggests that the 20 kV/cm NSEPs are sufficient to enhance the synergistic benefit with the antibiotics at 2 µg/mL, meaning that additional levels of the drugs do not provide benefit for the timescales assessed here. Applying the 30 kV/cm NSEPs induced 2-log reduction. Combining the 30 kV/cm NSEPs with 2 µg/mL of these antibiotics resulted in a statistically significant improvement to 3.5 to 5-log reduction and combining with 20 µg/mL resulted in 3.5 to 6-log reduction with the 6-log reduction involving the combination with rifampicin. FIG. 10B shows that 20 kV/cm NSEPs induce synergy for all the 2 µg/mL drugs except for vancomycin and for the 20 µg/mL only for linezolid and rifampicin. For the 30 kV/cm NSEPs, the drugs induced from between 1.5- to 4-log synergy. Thus, NSEPs again induce the gram-negative drugs to effectively inactivate a gram-positive bacterium.

Figure 11A:
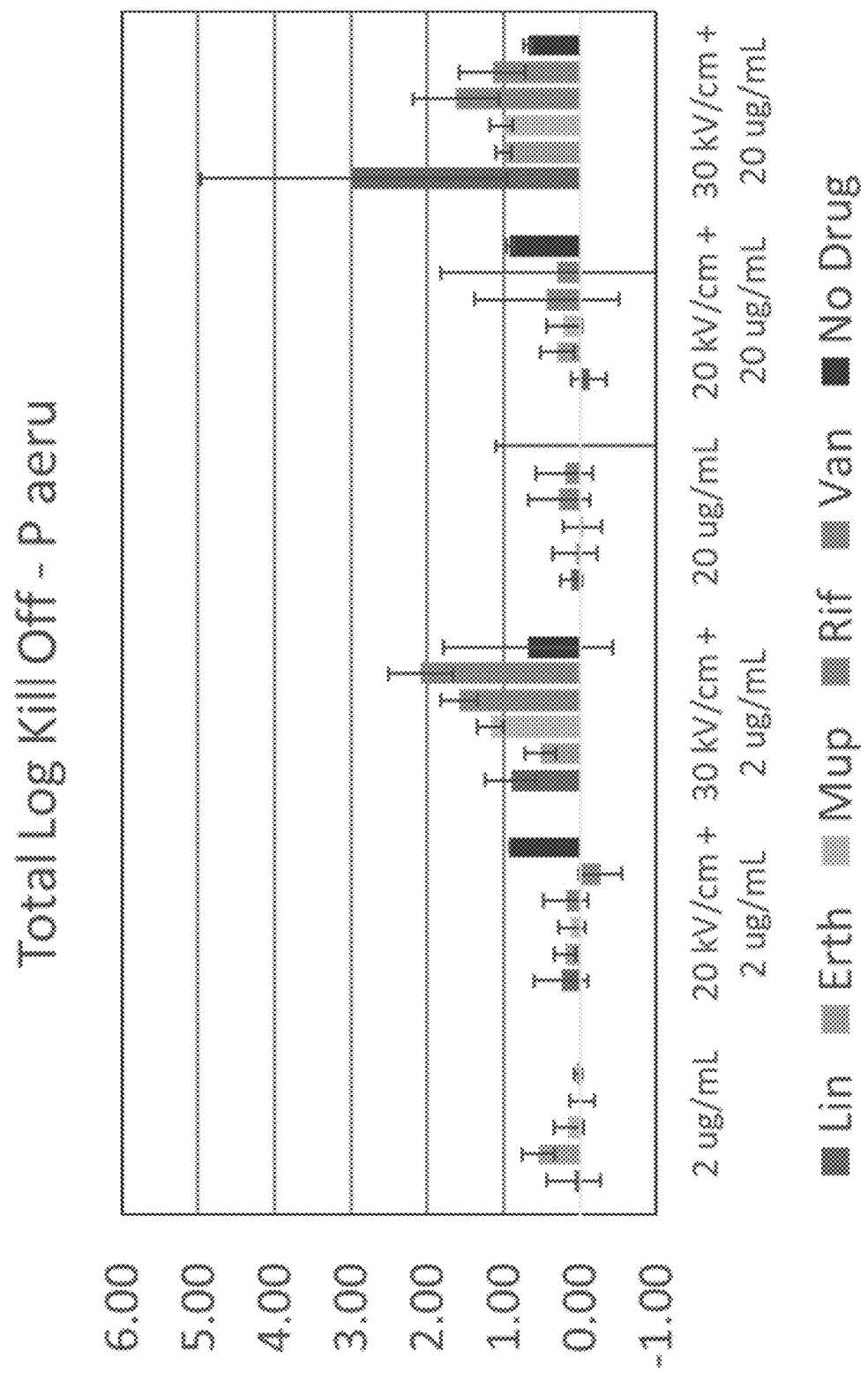
FIG. 11A and FIG. 11B show reduced amount of viable P. aeruginosa following treatment with 300 ns electric pulses (EPs) (445 at 20 kV/cm and 222 at 30 kV/cm) and/or various concentrations of antibiotics (from left to right, Lin=linezolid, Erth=erythromycin, Mup=mupirocin, Rif=rifampicin, and Van=vancomycin).
Figure 11B:
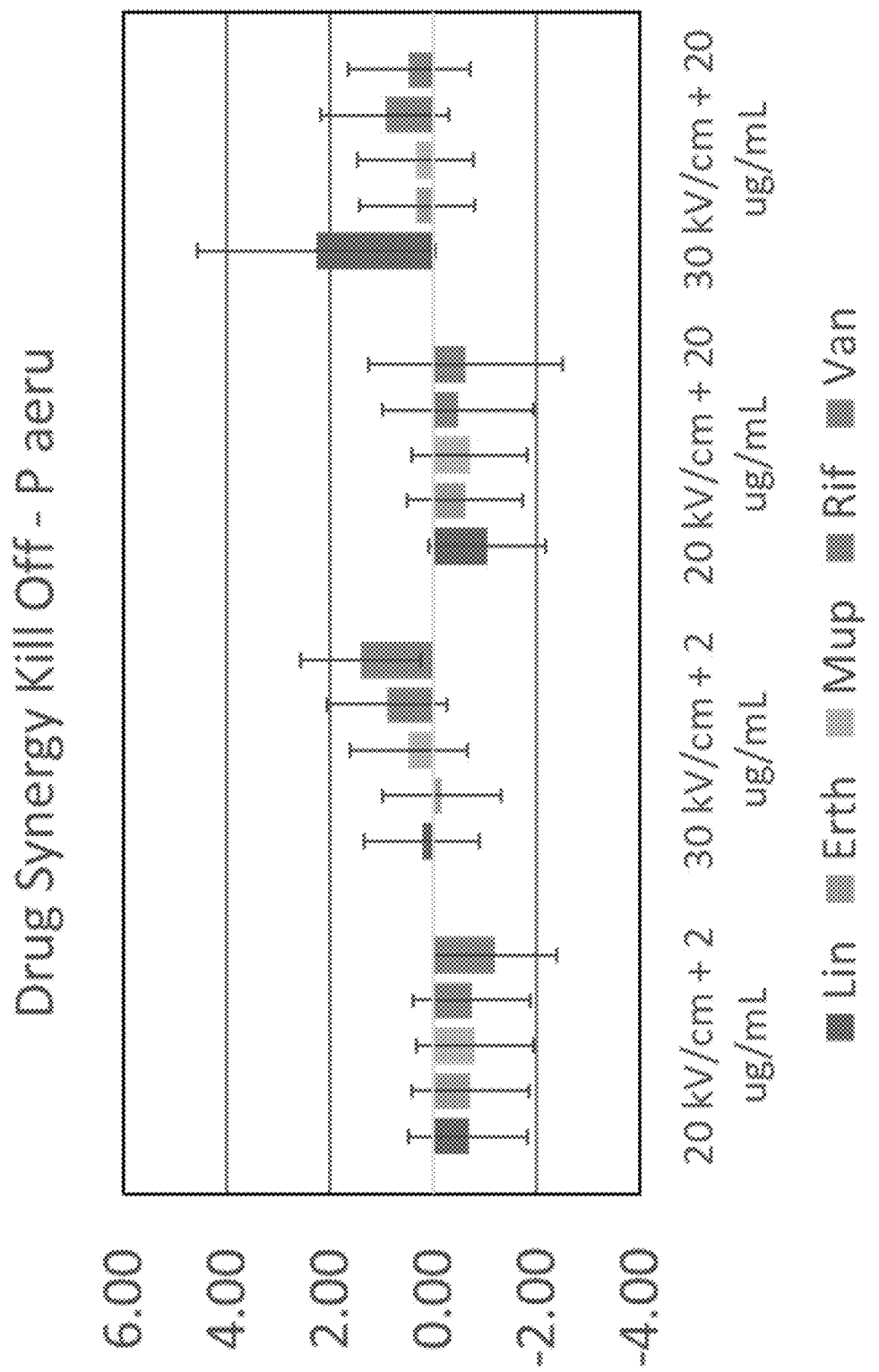

For P. aeruginosa, a biofilm forming bacteria, FIGS. 11A-11B show that the drugs alone induced no activation, the 20 kV/cm NSEPs induced approximately 1-log reduction, and the 30 kV/cm NSEPs induced less than 1-log reduction. In this case, combining 2 µg/mL or 20 µg/mL of linezolid, erythromycin, mupirocin, rifampicin, or vancomycin with the 20 kV/cm NSEPs induced no additional inactivation (and in several cases actually induced less inactivation). For the 30 kV/cm NSEPs, adding 2 µg/mL induced up to 2-log reduction for vancomycin. Combining 20 µg/mL with the 30 kV/cm NSEPs caused improvements in inactivation except for van.

FIG. 11B shows that combining 2 µg/mL of vancomycin leads to synergy with 30 kV/cm NSEPs. Results demonstrate an improvement when applying 30 kV/cm NSEPs compared to the 20 kV/cm NSEPs.

Although preferred embodiments have been depicted and described in detail herein, it will be apparent to those skilled in the relevant art that various modifications, additions, substitutions, and the like can be made without departing from the spirit of the present disclosure and these are therefore considered to be within the scope of the present disclosure as defined in the claims that follow.

What is claimed is:

1. A method of reducing a number of viable microbes, comprising: contacting microbes with an antibiotic compound and applying pulses of electricity having a duration of between about 50 nanoseconds and about 900 nanoseconds.

2. The method of claim 1, wherein the pulses of electricity have an intensity and the intensity is between about 20 kV/cm and about 40 kV/cm.

3. The method of claim 2, wherein the pulses of electricity are applied at a frequency of between about 0.1 Hz and about 10 Hz.

4. The method of claim 1, wherein said microbes are a strain of bacteria and the antibiotic is applied at a concentration for a duration, wherein applying the antibiotic to the strain at the concentration for the duration does not reduce a viable number of bacteria of the strain when the pulses of electricity are not also applied to the strain.

5. The method of claim 1, wherein the microbes comprise a gram-negative strain of bacteria.

6. The method of claim 1, wherein the microbes comprise a gram-positive strain of bacteria.

7. The method of claim 1, wherein said microbes are a strain of bacteria and the antibiotic is applied at a concentration for a duration, wherein the reducing is greater when the antibiotic is applied to the strain at the concentration for the duration when the pulses of electricity are applied to the strain than when the antibiotic is applied to the strain at the concentration for the duration when the pulses of electricity are not applied to the strain.

8. The method of claim 7, wherein microbes comprise a gram-negative strain of bacteria.

9. The method of claim 7, wherein the microbes comprise a gram-positive strain of bacteria.

10. The method of claim 1, wherein the antibiotic is selected from at least one of an aminoglycoside antibiotic, an ansamycin antiobiotic, a beta-lactam antibiotic, a glycopeptide antibiotic, a lincosamide antibiotic, a lipopeptide antibiotic, a macrolide antibiotic, a monobactam antibiotic, a nitrofuran antibiotic, an oxazolidinone antibiotic, a quinolone antibiotic, a fluoroquinolone antibiotic, a sulfonamide antibiotic, a tetracycline antibiotic, pexiganan, fusidic acid, mupirocin, and any combination of at least two of the foregoing.

11. The method of claim 1, wherein the antibiotic is selected from at least one of tobramycin, streptomycin, rifampicin, vancomycin, clindamycin, daptomycin, erythromycin, linezolid, penicillin, minocycline, pexiganan, fusidic acid, mupirocin, bacitracin, neomycin, polymixin B, metronidazole, silver, zinc, copper, and any combination of at least two of the foregoing.

12. The method of claim 1, wherein the microbe is *Staphylococcus aureus, Staphylococcus epidermidis, Escherichia coli, Acenitobacter baumanii, Klebsiella pneumoniae,* or *Pseudomonas aeruginosa.*

13. The method of claim 12, wherein the microbe is vancomycin-resistant *Staphylococcus aureus*, methicillin-resistant *Staphylococcus aureus*, a strain of multidrug-resistant *Pseudomonas aeruginosa*, or a strain of multidrug-resistant *Escherichia coli.*

14. A method of reducing a number of viable microbes, comprising: contacting microbes with an antibiotic compound and applying pulses of electricity having a duration of between about 50 nanoseconds and about 900 nanoseconds and an intensity of between about 20 kV/cm and about 40 kV/cm.

15. The method of claim 14, wherein the pulses of electricity are applied at a frequency of between about 0.1 Hz and about 10 Hz.

16. The method of claim 14, wherein the microbes comprise a gram-negative strain of bacteria.

17. The method of claim 14, wherein the microbes comprise a gram-positive strain of bacteria.

18. A method of reducing a number of viable microbes, comprising: contacting microbes with an antibiotic compound and applying pulses of electricity having a duration of between about 50 nanoseconds and about 900 nanoseconds and an intensity of between about 20 kV/cm and about 40 kV/cm, wherein the pulses of electricity are applied at a frequency of between about 0.1 Hz and about 10 Hz.

19. The method of claim 18, wherein the microbes comprise a gram-negative strain of bacteria.

20. The method of claim 18, wherein the microbes comprise a gram-positive strain of bacteria.

* * * * *